(12) United States Patent
Alvarez et al.

(10) Patent No.: US 9,359,415 B2
(45) Date of Patent: Jun. 7, 2016

(54) LIGANDS MODIFIED BY CIRCULAR PERMUTATION AS AGONISTS AND ANTAGONISTS

(71) Applicant: Alkermes, Inc., Waltham, MA (US)

(72) Inventors: Juan Alvarez, Chelmsford, MA (US); Jean Chamoun, Waltham, MA (US)

(73) Assignee: Alkermes, Inc., Waltham, MA (US)

( * ) Notice: Subject to any disclaimer, the term of this patent is extended or adjusted under 35 U.S.C. 154(b) by 0 days.

(21) Appl. No.: 13/911,827

(22) Filed: Jun. 6, 2013

(65) Prior Publication Data

US 2013/0336924 A1 Dec. 19, 2013

Related U.S. Application Data

(60) Provisional application No. 61/567,378, filed on Jun. 8, 2012, provisional application No. 61/723,081, filed on Nov. 6, 2012, provisional application No. 61/657,264, filed on Jun. 8, 2012, provisional application No. 61/778,575, filed on Mar. 13, 2013, provisional application No. 61/657,285, filed on Jun. 8, 2012, provisional application No. 61/778,812, filed on Mar. 13, 2013.

(51) Int. Cl.

| C07K 19/00 | (2006.01) |
|---|---|
| C07K 14/47 | (2006.01) |
| C07K 14/545 | (2006.01) |
| C07K 14/54 | (2006.01) |
| C07K 14/55 | (2006.01) |
| C07K 14/715 | (2006.01) |
| C07K 14/50 | (2006.01) |
| C07K 14/705 | (2006.01) |
| C07K 14/71 | (2006.01) |

(52) U.S. Cl.
CPC ......... *C07K 14/4713* (2013.01); *C07K 14/4727* (2013.01); *C07K 14/50* (2013.01); *C07K 14/545* (2013.01); *C07K 14/5412* (2013.01); *C07K 14/5443* (2013.01); *C07K 14/55* (2013.01); *C07K 14/70503* (2013.01); *C07K 14/71* (2013.01); *C07K 14/7155* (2013.01); *C07K 2319/00* (2013.01); *C07K 2319/02* (2013.01); *C07K 2319/30* (2013.01); *C07K 2319/91* (2013.01)

(58) Field of Classification Search
None
See application file for complete search history.

(56) References Cited

U.S. PATENT DOCUMENTS

| 5,635,599 | A | 6/1997 | Pastan et al. |
|---|---|---|---|
| 6,011,002 | A | 1/2000 | Pastan et al. |
| 6,492,492 | B1 | 12/2002 | Stayton |
| 6,518,061 | B1 | 2/2003 | Puri et al. |
| 8,734,774 | B2 * | 5/2014 | Frelinger et al. ............. 424/85.1 |
| 2002/0159969 | A1 | 10/2002 | Agrawal et al. |
| 2003/0073822 | A1 | 4/2003 | Lofling et al. |
| 2003/0165825 | A1 | 9/2003 | Balint et al. |
| 2004/0002585 | A1 | 1/2004 | Holgersson |
| 2004/0137580 | A1 | 7/2004 | Holgersson et al. |
| 2004/0175359 | A1 | 9/2004 | Desjarlais et al. |
| 2007/0105767 | A1 | 5/2007 | Kharbanda et al. |
| 2007/0264234 | A1 | 11/2007 | Sayers et al. |
| 2008/0003619 | A1 | 1/2008 | Lutz et al. |
| 2008/0241166 | A1 | 10/2008 | Tomlinson et al. |
| 2008/0286211 | A1 | 11/2008 | Barker |
| 2008/0300193 | A1 | 12/2008 | Ahn et al. |
| 2009/0005266 | A1 | 1/2009 | Ostermeier et al. |
| 2010/0035804 | A1 | 2/2010 | Pradhananga et al. |
| 2010/0036001 | A1 | 2/2010 | DeAngelis |
| 2010/0063258 | A1 | 3/2010 | Swartz et al. |
| 2010/0196991 | A1 | 8/2010 | O'Connell et al. |
| 2010/0261872 | A1 | 10/2010 | DeFrees et al. |
| 2010/0298236 | A1 | 11/2010 | Grotzinger et al. |
| 2012/0028911 | A1 | 2/2012 | Shebuski et al. |
| 2013/0040845 | A1 | 2/2013 | Springer et al. |

FOREIGN PATENT DOCUMENTS

| WO | 9527732 A2 | 10/1995 |
|---|---|---|
| WO | 9629417 A1 | 9/1996 |
| WO | 9818924 A1 | 5/1998 |
| WO | 9818926 A1 | 5/1998 |
| WO | 0196565 A2 | 12/2001 |
| WO | 0222149 A1 | 3/2002 |
| WO | 03059376 A1 | 7/2003 |
| WO | 2004033651 A2 | 4/2004 |
| WO | 2005003165 A2 | 1/2005 |
| WO | 2007046006 A2 | 4/2007 |
| WO | 2007128979 A1 | 11/2007 |
| WO | 2008072075 A2 | 6/2008 |
| WO | 2010020766 A2 | 2/2010 |
| WO | 2011123683 A2 | 10/2011 |
| WO | 2012016203 A1 | 2/2012 |

OTHER PUBLICATIONS

Jones, D., et al., "Developing Therapeutic Proteins by Engineering Ligand-Receptor Interactions," Trends in Biotechnology 26(9): pp. 498-505 (2008).

Yu, Y., et al., "Circular Permutation: A Different Way to Engineer Enzyme Structure and Function," Trends in Biotechnology 29(1): pp. 18-25 (Jan. 2011).

Heaney, M., et al., "Soluble Cytokine Receptors," Blood, The Journal of the American Society of Hematology, 87(3): pp. 847-857 (Feb. 1996).

UniProt Protein Database, Protein Accession Q8N307, MUC20 or Mucin-20, Sequence on pp. 6-7, accessed on Nov. 20, 2014.

(Continued)

*Primary Examiner* — Michael Pak
(74) *Attorney, Agent, or Firm* — Elmore Patent Law Group, PC.; Darlene A. Vanstone; Carolyn S. Elmore

(57) ABSTRACT

The present invention provides fusion polypeptides comprising polypeptide ligands that are modified by circular permutation and fused to at least one polypeptide fusion partner wherein such fusion polypeptides have new, improved or enhanced biological functions or activities. Such improvements include, but are not limited to, increased binding affinity, increased activity, increased agonist activity (super agonist), antagonist activity, increased accessibility, increased flexibility of the active site, increased stability, broader and/or changed substrate specificity, and combinations thereof.

3 Claims, 13 Drawing Sheets

(56) References Cited

OTHER PUBLICATIONS

Thornton, D.J., et al., "From Mucins to Mucus Towards a More Coherent Understanding of this Essential Barrier," Proc Am Thorac Soc., vol. 1, pp. 54-61 (2004).

Lang, T., et al., "Bioinformatic Identification of Polymerizing and Transmembrane Mucins in the Puffer Fish *Fugu rubripes*," Glycobiology 14(6): pp. 521-527 (2004).

Antibody Structure and Classification-Note 7.1, Molecular Probes the Handbook, www.invitrogen.com, retrieved from the Internet, Nov. 2011.

Interleukin 1 receptor antagonist, Wikipedia, the free encyclopedia, retrieved from the Internet, Nov. 2011.

Anakinra, Wikipedia, The free encyclopedia, retrieved from the Internet, Nov. 2011.

Arai, et al., "Design of the Linkers Which Effectively Separate Domains of a Bifunctional Fusion Protein," Protein Engineering 14(8): pp. 529-532 (Sep. 2001).

Wriggers, et al., "Control of Protein Functional Dynamics by Peptide Linkers," Biopolymers (Peptide Science) 80: pp. 736-746 (May 2005).

Zhang, et al., "Design and Optimization of a Linker for Fusion Protein Construction," Progress in Natural Science 19: pp. 1197-1200 (Sep. 2009).

\* cited by examiner

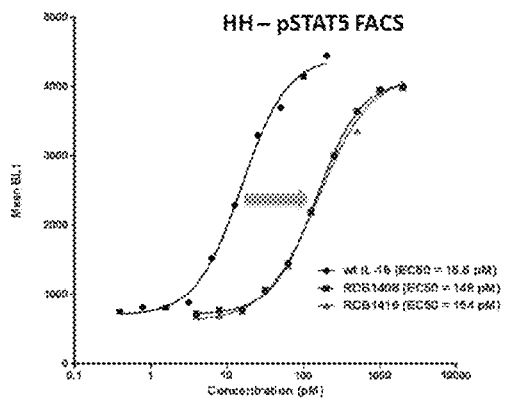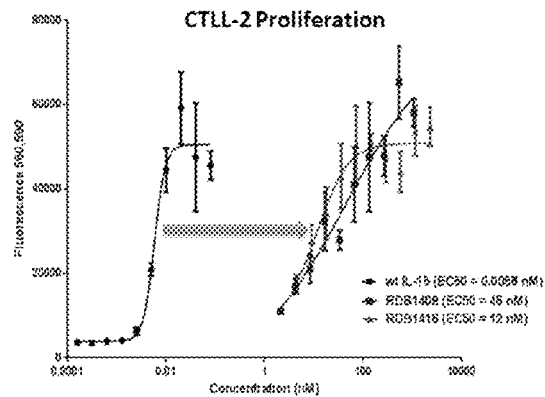
FIG. 12A  FIG. 12B
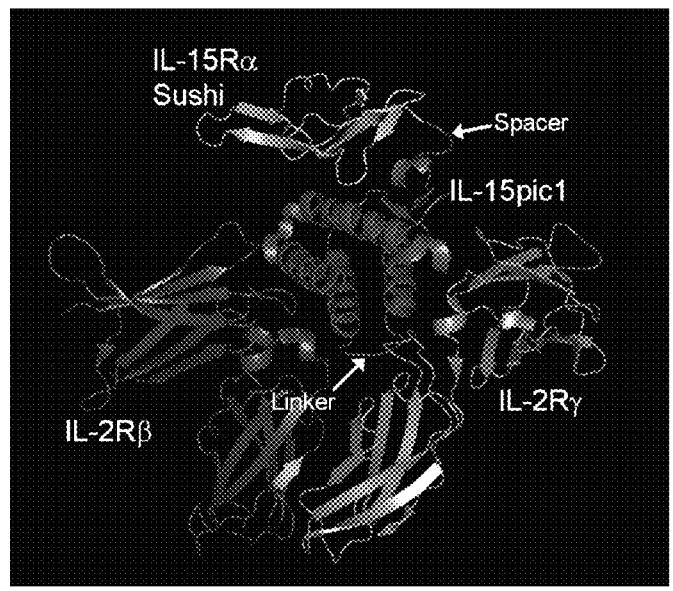
FIG. 13

LIGANDS MODIFIED BY CIRCULAR PERMUTATION AS AGONISTS AND ANTAGONISTS

RELATED APPLICATIONS

This application claims the benefit of U.S. Provisional Application Nos. 61/657,378, filed on Jun. 8, 2012; 61/723,081, filed Nov. 6, 2012; 61/657,264, filed Jun. 8, 2012; 61/778,575, filed Mar. 13, 2013; 61/657,285, filed Jun. 8, 2012 and 61/778,812, filed Mar. 13, 2013. The entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on May 31, 2013, is named 4000.3059WO_SL.txt and is 66,878 bytes in size.

BACKGROUND OF THE INVENTION

Ligand-receptor interactions are essential to a number of cell signaling pathways. Growth factors, cytokines and other regulatory proteins use these interactions to mediate cell responses. Proteins that inhibit or facilitate these processes have potential as therapeutics.

Given some of the drawbacks of monoclonal antibody approaches to inhibiting ligand-receptor functions such as expensive manufacturing, large size, limited penetration into tissues and undesirable side effects, researchers have been focusing on the use of non-antibody proteins as therapeutic agents. Furthermore, therapeutic antibody strategies are generally limited to inhibiting, or antagonizing, a signaling pathway and not competent to strategies to enhance, or agonize, a pathway. Thus, new protein engineering approaches are being explored to develop ligands and receptors as agonists and antagonists of clinically important targets as an alternative to antibody strategies.

Circular permutation involves the linking of the native amino and carboxy ends of a protein, generally with a linker, and creating new amino and carboxy termini by cleaving at a new site within the protein sequence, generally a loop; such that the primary sequence of the resulting protein is reordered, while the secondary structure (and activity) is retained. Thus, creation of the new termini may provide better locations for attachment of a fusion partner relative to the native termini.

Circular permutation of a protein ligand provides a means by which a protein may be altered to produce new carboxyl and amino termini without diminishing the specificity and binding affinity of the altered protein ligand for its target relative to its native form. Additionally, the new termini can be preferentially moved to a location preferential for incorporating the circularly permuted ligand into a fusion polypeptide, and demonstrate better activity compared with a fusion polypeptide containing the native (non-circularly permuted) ligand.

The present invention provides fusion polypeptides comprising ligands modified by circular permutation which function as agonists, super agonists or antagonists of a signaling pathway. Such fusion polypeptides are beneficial in the treatment of many disorders, conditions, and diseases that rely on ligand-receptor interaction and signal transduction. For example, such fusion polypeptides that act as antagonists of a target receptor have potential as therapeutics for cancer and autoimmune disorders. Such fusion polypeptides that act as agonists or superagonists of a signaling pathway have the potential, for example, in cancer or regenerative medicine.

SUMMARY OF THE INVENTION

The present invention provides fusion polypeptides comprising polypeptide ligands that are modified by circular permutation and fused to at least one polypeptide fusion partner wherein such fusion polypeptides have new, improved or enhanced biological functions or activities relative the analogous fusion protein with the native (non-circularly permuted) ligand. Such improvements include, but are not limited to, increased binding affinity, increased activity, increased agonist activity (super agonist), increased antagonist activity, increased accessibility, increased flexibility of the active site, increased stability, broader and/or changed substrate specificity, enhanced tissue targeting, enhanced protein binding, enhanced membrane targeting, improved pharmacokinetic parameters, improved physical properties, and combinations thereof.

In one embodiment, the circularly permuted ligands comprise all or any portion of their native polypeptide chains, and may optionally include linkers. The circularly permuted ligands of the invention are designed to be optimally oriented such that they may be fused to at least one desired polypeptide fusion partner without compromising the activity, such as the binding affinity of the modified ligand for its target. In one embodiment, the circularly permuted (modified) ligands of the fusion polypeptides are at least as active, and are preferably more active, as compared to their corresponding native proteins. In one embodiment the fusion proteins of the invention have a greater binding affinity for their targets proteins. In one embodiment the binding affinity of the fusion protein for its target protein is at least 5-fold, preferably at least 10-fold, preferably at least 20 fold or more greater than the affinity of the native ligand for the protein target. In one embodiment the fusion polypeptide of the invention has at least 10 fold greater binding affinity for the receptor.

In one embodiment, the ligands are selected from the group including, but not limited to, cytokines, lymphokines, chemokines, adipokines, growth factors, hormones, cell adhesion molecules and neurotransmitters. Polypeptide fusion partners may be any polypeptide that provides and enhancement to the native protein. For example, fusion partners may be selected from the group including, but not limited to, all or a portion of: glycoproteins, proteoglycans, cell signaling molecules, accessory proteins, soluble receptors, membrane bound receptors, transmembrane receptors, antibodies, enzymes, targeting polypeptides (e.g., nanobodies), mucins or mucin-like peptides, synthetic polypeptides or any combinations thereof. Enhancements include, but are not limited to, improvements in affinity, agonism, antagonism, addition of synergistic functional activity, tissue targeting, protein targeting, membrane targeting, pharmacokinetic parameters (eg. half life), or physical properties (eg. solubility).

In a preferred embodiment, at least one polypeptide fusion partner comprises all or a portion of a subunit of the target receptor or another molecule involved in its natural signal transduction pathway. It is understood that a polypeptide fusion partner may comprise a polypeptide that is at least 60%, at least 70%, at least 80% or at least 90% homologous to all or a portion of a subunit of a target receptor or another molecule involved in a signal transduction pathway.

In one embodiment, the invention provides for fusion polypeptides comprising a modified ligand and a polypeptide fusion partner that are further linked to a second fusion partner. Examples of second fusion partners include all or any portion of an antibody (e.g. the Fc region of an antibody) and any of the types of polypeptides suitable as a first fusion partner described above.

In a preferred embodiment, the fusion polypeptides of the invention function as new and improved agonists (super agonists), or antagonists of a receptor such as a cellular receptor that is involved in signal transduction of a cell signaling pathway. In a preferred embodiment, the fusion polypeptides of the invention can bind a monomeric, dimeric, or a multimeric target receptor and can inhibit or enhance dimerization, trimerization or multimerization of the receptor and/or inhibit or enhance signal transduction and downstream signaling of a cellular pathway.

In one embodiment, the invention provides a fusion polypeptide comprising, a first polypeptide fusion partner linked to a modified ligand corresponding to a native ligand specific for a target receptor, wherein the modified ligand has been circularly permuted to create a new N-terminus and a new C-terminus as compared to the native ligand, and wherein the new N-terminus or the new C-terminus of the modified ligand is linked to a first polypeptide fusion partner to form a fusion polypeptide that optionally has increased affinity for the target receptor as compared to the native ligand for the receptor, and wherein upon association of the fusion polypeptide with the target receptor the fusion polypeptide super agonizes or antagonizes the activity of the target receptor. In one embodiment, the new C-terminus and the new N-terminus of the modified ligand do not disrupt any binding domain of the modified ligand for the target receptor.

In one embodiment, the target receptor functions by stepwise formation of a multimeric activation complex to trigger signal transduction of a signaling cellular pathway and wherein upon binding of the fusion polypeptide to the receptor, signal transduction is super agonized or antagonized.

In one embodiment, the fusion polypeptide binds the receptor and enhances the stepwise formation of the multimeric activation complex thereby super agonizing signal transduction by the target receptor.

In one embodiment, the fusion polypeptide binds the receptor and sterically hinders the stepwise formation of the multimeric complex thereby antagonizing signal transduction by the target receptor.

In one embodiment the fusion polypeptide comprises the modified ligand and a first fusion partner wherein the first fusion partner of the modified ligand is derived from all or a portion of the protein with which the native ligand of the target receptor would have associated in the first step of the stepwise formation of the receptor's multimeric activation complex. In one embodiment the fusion polypeptide comprises the modified protein and a fusion partner wherein the fusion partner of the modified protein is derived from all or a portion of the protein with which the native protein of the target receptor would have associated in downstream steps of the stepwise formation of the receptor's multimeric activation complex.

In one embodiment the first fusion partner of the heterodimer is fused to the modified ligand in a position that is oriented to enhance the stepwise formation of the receptor's multimeric activation complex.

In one embodiment, the first fusion partner of the heterodimer is fused to the modified ligand in a position that is oriented to sterically hinder the formation of the receptor's multimeric activation complex.

In one embodiment the fusion polypeptide is a homodimer comprising the modified protein and a fusion partner wherein the fusion partner of the modified ligand is derived from all or a portion of the same ligand where homodimerization is required for formation of the receptor's multimeric activation complex.

In one embodiment the invention provides a pharmaceutical composition comprising the fusion polypeptide of the invention and a pharmaceutically acceptable carrier.

In one embodiment the invention provides an isolated or recombinant nucleic acid encoding the fusion polypeptide of the invention; a recombinant vector comprising the nucleic acid encoding a fusion polypeptide of the invention and a host cell comprising a vector of the invention.

In one embodiment the invention provides a method of super agonizing a target receptor comprising the step of contacting the receptor with the fusion polypeptide of the invention.

In one embodiment the invention provides a method of antagonizing a target receptor comprising the step of contacting the receptor with a fusion polypeptide of the invention.

In one embodiment, the invention provides a method of making a fusion polypeptide of the invention comprising the steps of: a) selecting a native ligand that binds to a receptor wherein the receptor functions by stepwise formation of a multimeric activation complex to trigger signal transduction of a signaling cellular pathway; b) creating a modified ligand by circular permutation to provide a modified ligand having new N-terminus and a new C-terminus as compared to the native ligand of step (a); and c) linking a first polypeptide fusion partner to the N- or C-terminus of the modified ligand of step (b) to make a fusion polypeptide, wherein the new N- or C-termini of the modified ligand are located to permit the first fusion partner to be linked to the modified ligand in a position oriented to antagonize or super agonize the function of the target receptor upon binding of the fusion polypeptide to the target receptor. In one embodiment, the method further comprises fusing a second fusion partner to the modified ligand of step (b) wherein the second fusion partner provides an additional enhancement to the protein, such as extending the half-life of the fusion polypeptide in vivo. Other enhancements that could be engineered via step (c) include, but are not limited to, addition of synergistic functional activity, organ targeting, tissue targeting, protein targeting, membrane targeting, biological matrix targeting, pharmacokinetic (e.g. percent bioavailability) or physical properties (e.g. solubility).

BRIEF DESCRIPTION OF THE DRAWINGS

FIG. 7A) and a modeled representation of the potential complex formation mediated by RDB1538 (CP_IL-1βIL-1RI (D1-D2); FIG. 7B). IL-1β (highlighted with an arrow in the structure) binds to receptors IL-1RI (black, coming out of the plane) and IL-1RAcP (light grey, going away from the plane). The native N and C termini of IL-1β are not in close proximity to the C-terminus of D1-D2 domain of IL-1RI. The termini of the engineered circularly permuted IL-1β are now proximal to the C-terminus of D1-D2 domain of IL-1 RI, thus facilitating the generation of the fusion protein. The shaded area highlights the linker connecting the circularly permuted IL-1β variant to IL-1RI receptor.

FIG. 8A) and modeled signaling complex mediated by RDB1405 (CP_IL-2_IL-2Rα; FIG. 8B). IL2 (highlighted with an arrow in the structure) binds to receptors IL2Rα (grey, top left in the complex), IL2Rβ (light grey, bottom left in the complex) and $γ_c$ (black, bottom right in the complex). IL-2Rα stabilizes the conformation of IL-2 to enhance its binding affinity to IL-2Rβ. The native N and C termini of IL-2 are on the face distal to IL-2/IL-2Rα interface. The termini of the engineered circularly permuted IL-2 are now proximal to the IL-2/IL-2Rα interface, thus facilitating the generation of the fusion protein. The shaded area highlights the linker connecting the circularly permuted IL-2 variant to IL-2Rα receptor.

FIGS. 12A and 12B Response of HH cells (left) and CTLL-2 cells (right) to wild-type IL-15 and engineered IL-15 variants.

FIG. 13. Structure of the modeled IL-15 signaling complex for the CP-IL-15-IL-15Rα fusion proteins generated by superposition of the IL-15/IL-15Rα complex (2Z3Q.pdb) onto the IL-Rβ and IL-2Rγ chains from the IL-2 ternary signaling complex structure, 2ERJ.pdb). The 'Linker' joining the native termini of IL-15 to create the circularly permuted IL-15 variant and 'Spacer' to create the CP-IL-15-IL-15Rα fusion are highlighted with arrows. Note that the native termini of IL-15 (originally located at the 'Linker' site) are far distally oriented from the IL-15Rα binding interface, thus creating the need for circular permutation of the ligand.

DETAILED DESCRIPTION OF THE INVENTION

Figure 1:
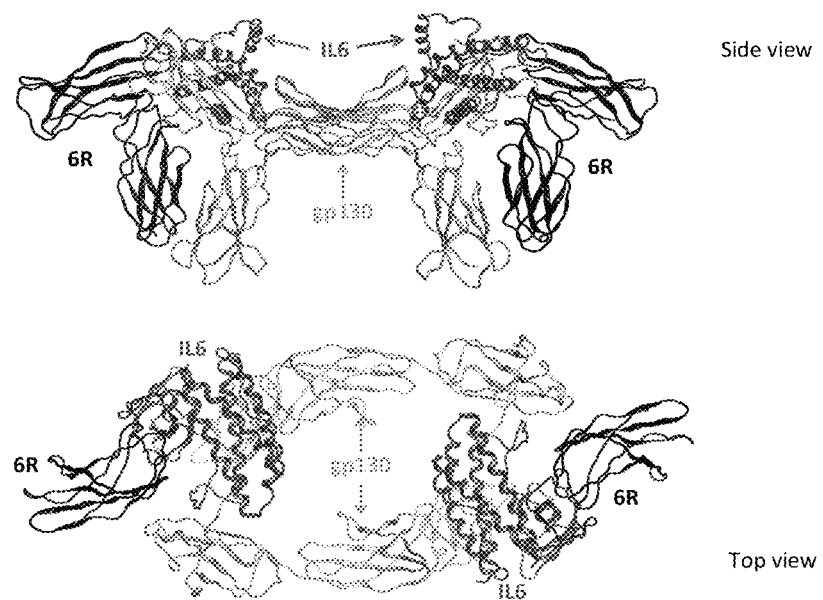
FIG. 1. Structure of the human IL6 hexameric signaling complex (PDB: 1P9M). Side view (top) and top view (bottom) of the hexameric complex consisting of two IL-6 molecules (dark grey), two soluble IL-6Rα molecules (D2-D3 of IL6 receptor subunit a black), and two soluble gp130 molecules (D1-D2-D3, light grey).

A description of preferred embodiments of the invention follows. For illustrative purposes, polypeptide fusion proteins of the invention featuring a circularly permutated IL-6 ligand fused to a portion of gp130 is used as an exemplary fusion polypeptide of the invention. It is understood that the biological functions, activities and other features of the described embodiments are generally applicable to other fusion polypeptides in accordance with the invention comprising ligands modified by circular permutation fused to polypeptide fusion partners.

As used in the specification and the appended claims, the singular forms "a," "an" and "the" include plural referents unless the context clearly dictates otherwise. Thus, for example, reference to "a polypeptide fusion partner" includes a plurality of polypeptide fusion partners. In this specification and in the claims that follow, reference will be made to a number of terms that shall be defined to have the following meanings, unless a contrary intention is apparent.

DEFINITIONS

The terms "circular permutation" and "circularly permuted" "(CP)" as used herein, refers to the conceptual process of taking a linear protein, or its cognate nucleic acid sequence, and fusing the native N- and C-termini (directly or through a linker, using protein or recombinant DNA methodologies) to form a circular molecule, and then cutting (opening?) the circular molecule at a different location to form a new linear protein, or cognate nucleic acid molecule, with termini different from the termini in the original molecule. Circular permutation thus preserves the sequence, structure, and function of a protein (other than the optional linker), while generating new C- and N-termini at different locations that, in accordance with one aspect of the invention, results in an improved orientation for fusing a desired polypeptide fusion partner as compared to the original ligand. Circular permutation also includes any process that results in a circularly permutated straight-chain molecule, as defined herein. In general, a circularly permuted molecule is de novo expressed as a linear molecule and does not formally go through the circularization and opening steps. The particular circular permutation of a molecule, herein, is designated by brackets containing, in the case of a circularly permuted protein, the amino acid residues between which the peptide bond is eliminated. For example, the designation IL6(Q182/Q180) designates a circularly permuted IL6 growth factor in which the opening site (position at which the peptide bond is eliminated) occurred between residues Q182 and Q180 of the unpermuted or unmodified native IL6, and thus the newly created N-terminus is a Glutamine which was formerly residue 182, and the newly created C-terminus is a Glutamine which was formerly residue 180.

A "spacer" as used herein and refer to a peptide that joins the proteins comprising a fusion protein. Generally the spacer has no specific biological activity and its purpose is merely to join the proteins or to preserve some minimum distance or other spatial relationship between them. However, the constituent amino acids of a spacer may be selected based on some properties of the linker or of the resulting molecule such as the flexibility, hydrophilicity, net charge, or proteolytic susceptibility or lack thereof, and lack of immunogenicity.

The terms "unpermuted", "native", "wild type", or "unmodified" ligand, polypeptide, protein, cytokine, or growth factor, are used herein to provide a reference point for the ligand, cytokine, growth factor or protein prior to its rearrangement into a circularly permuted molecule, as described above. Typically, the unmodified ligand, growth factor or protein has amino and carboxy termini and an amino acid sequence that correspond substantially to the amino and carboxy termini and amino acid sequence of the ligand, growth factor, or protein, or an independent domain of a protein, as it generally occurs in vivo. The unmodified ligand, growth factor, or protein may be a fully mature form or a precursor to the mature form (such as a pro-protein).

The term "ligand" is used herein generally to denote any polypeptide (whether native, endogenous, or modified in accordance with the invention) that binds to a second protein or receptor and is a component of a biochemical pathways. A ligand directly or indirectly may affect (e.g., induce, inhibit) receptor activity (e.g., signaling, adhesion).

The term "modified ligand" is used herein to indicate a ligand that has been modified by circular permutation as compared to the corresponding native ligand.

"Activity" or "biological activity" refer to an in vitro or in vivo biological function or effect, including but not limited to receptor binding, antagonist activity, agonist activity, or a cellular or physiologic response.

An "agonist" is a fusion polypeptide of the invention which is capable of binding to a desired receptor to result in an activated receptor complex. A "superagonist" is a fusion polypeptide of the invention capable of binding the target receptor and that provides enhanced activation of the receptor complex as compared to the native ligand for that target receptor. Activation by the fusion polypeptide superagonist of the invention may be enhanced at least two-fold, and preferably at least 5-fold, preferably at least 10-fold or preferably at least 20-fold or more as compared to activation of the target receptor by the native ligand. A fusion polypeptide of the invention "having agonist activity" refers to the fact that the fusion polypeptides are able to bind to and activate or superagonize at least one receptor.

An "antagonist" is a fusion polypeptide of the invention which is capable of binding to a desired receptor but incapable of mediating correct conformational or molecular assembly changes of the receptor molecules necessary to result in an activated complex, and whereby native ligand-mediated receptor activation is substantially inhibited. Receptor activation upon binding of a suitable ligand generally involves either a conformational change in the receptor or a difference in association states of the receptor, e.g. oligomerisation of receptor subunits or recruitment of additional proteins or receptors.

The term "receptor" is understood to indicate a protein present on a cell surface (or a soluble receptor not present on the cell surface but which has or associates with a counterpart cell surface receptor) with which a ligand binds. Cell surface receptors are typically composed of different domains or subunits with different functions, such as an extracellular domain (or domains) containing the region with which the ligand interacts, a transmembrane domain or domains (or in some cases an anchoring lipid) which anchors the receptor in the cell membrane. In some cases an intracellular effector domain which initiates a cellular signal in response to ligand binding (signal transduction) is also present. Soluble receptors are typically composed of one or more of the extracellular domains resulting from protolytic cleavage from the membrane anchoring region.

"Target receptors" or "Target ligands" according to the invention are the molecules to which the fusion-polypeptides of the invention are designed to directly bind. In one embodiment "target receptors" according to the invention are capable of ultimately binding or otherwise associating with, signaling molecules (e.g. ligands) in triggering signal transduction of a signaling cellular pathway.

A receptor that is activated by the "stepwise formation of a multimeric activation complex" is a receptor that in addition to the binding of one or more ligands, requires the interaction of one or more additional protein subunits in a process known as dimerization, trimerization, multimerization, complexation, or oligomerization (also referred to in the art as "clustering") to fully achieve signal transduction of a cell signaling pathway. The receptor may already be in the form of a dimer or multimer prior to ligand binding and upon ligand binding may recruit additional soluble or membrane-anchored proteins in a stepwise fashion to build the fully functioning multimeric activation complex.

The "hydrodynamic radius" is the apparent radius ($R_h$ in nm) of a molecule in a solution calculated from diffusional properties. The "hydrodynamic radius" of a protein affects its rate of diffusion in aqueous. The hydrodynamic radius of a protein is influenced by its molecular weight as well as by its structure, including shape and compactness, and its hydration state. Methods for determining the hydrodynamic radius are well known in the art, such as by the use of DLS and size exclusion chromatography. Most proteins have globular structure, which is the most compact three-dimensional structure a protein can have with the smallest hydrodynamic radius. Some proteins adopt a random and open, unstructured, or 'linear' conformation and as a result have a much larger hydrodynamic radius compared to typical globular proteins of similar molecular weight.

A "mucin-domain polypeptide" is defined herein as any protein comprising a "mucin domain". A mucin domain is rich in potential glycosylation sites, and has a high content of serine and/or threonine and proline, which can make up greater than 40% of the amino acids. A mucin domain is heavily glycosylated with predominantly O-linked glycans.

The term "linker" or "linker sequence" as used herein, refers to the peptidic sequence that is used to join the amino and carboxy termini of a protein (or its corresponding nucleic acid sequence encoding the protein) through covalent bonds to both the amino and carboxy terminus. In some embodiments, the circularly permuted protein is produced by linking the ends of the corresponding DNA or RNA sequence, forming various permutants by cutting the circularized nucleic acid sequence, and subsequently translating the nucleic acid sequences to form the circularly permuted protein(s).

The term "residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "opening site", as used herein when referring to circular permutation, refers to the position at which a peptide bond would be eliminated to form new amino and carboxy termini, whether by protein or nucleic acid manipulation. The opening site is designated by the positions of the pair of amino acids, located between the amino and carboxy termini of the unpermuted (native) protein that become the new amino and carboxy termini of the circularly permuted protein. For example, in IL6 (Q182/Q180), the newly created N-terminus (the new starting point of the circularly permuted IL-6) is equivalent (structurally) to Q182 of native IL-6 and the newly created C-terminus (the last residue of the circularly permuted IL-6) is equivalent (structurally) to Q180 of native IL-6. Residue 181 of native IL-6 was eliminated in creating the opening site.

The term "polypeptides" and "protein" are used interchangeably herein and include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

All amino acid positions described herein use as a frame of reference sequences for the native protein. For example, native IL-1β (SEQ ID NO:19), native IL-6 (SEQ ID NO:3), native IL-2 (SEQ ID NO:20), native gp130 (SEQ ID NO:21), native IL-1RI (SEQ ID NO:22), and native IL-2Rα (SEQ ID NO:23) as presented in the Sequence Listing. For example, an IL-6 molecule "comprising amino acids 47 to 212" would refer to a molecule having amino acids substantially corresponding to those positions in SEQ ID NO:3. Other common references are used herein to indicate deletions or substitutions to a sequence using as reference sequences, the respective native sequences as referenced in the sequence listing or whose GenBank accession number is provided herein. Amino acid substitutions may be indicated by parentheses, for example "(Ser 287)" refers to a molecule having serine at amino acid position 287. Circularly permuted molecules are designated by the native molecule followed by brackets enclosing the amino acid positions that comprise the opening site. Thus, for example, IL6 (182/180) designates a circularly permuted IL6 in which the new amino terminus is at amino acid residue 182, and the new carboxy terminus is at amino acid residue 180 of the unpermuted native IL6. It is recognized that some substitutions, addition, or deletions may be made to any sequences described herein that do not alter the biological activity of the region. Indeed, some such modifications may be required to achieve expression of a particular protein. Thus, for example, a methionine may be added to a sequence to provide an initiator.

"Variant" refers to a polypeptide that differs from a reference polypeptide, but retains essential properties. A typical variant of a polypeptide differs in its primary amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. In addition, the term "variant" as used herein includes circular permutations of proteins and peptides.

The term "antibody", as used herein, includes various forms of modified or altered antibodies, such as an intact immunoglobulin, an Fc fragment comprising the constant region of the heavy chains, an Fv fragment containing only the light and heavy chain variable regions, an Fv fragment linked by a disulfide bond an Fab or (Fab)'$_2$ fragment containing the variable regions and parts of the constant regions, a single-chain antibody and the like.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease in humans or other animals, or to otherwise enhance physical or mental well being of humans or animals, caused by a fusion protein of the invention other than the ability to induce the production of an antibody against an antigenic epitope possessed by the active protein. Determination of a therapeutically effective amount is well within the capability of those skilled in the art, especially in light of the detailed disclosure provided herein.

The terms "therapeutically effective amount" and "therapeutically effective dose", as used herein, refers to an amount of a active protein, either alone or as a part of a fusion protein composition, that is capable of having any detectable, beneficial effect on any symptom, aspect, measured parameter or characteristics of a disease state or condition when administered in one or repeated doses to a subject. Such effect need not be absolute to be beneficial.

The term "therapeutically effective dose regimen", as used herein, refers to a schedule for consecutively administered doses of a active protein, either alone or as a part of a fusion protein composition, wherein the doses are given in therapeutically effective amounts to result in sustained beneficial effect on any symptom, aspect, measured parameter or characteristics of a disease state or condition.

As used herein, the term "dose" refers to the quantity of fusion polypeptide of the invention administered to a subject all at one time (unit dose), or in two or more administrations over a defined time interval. For example, dose can refer to the quantity of fusion polypeptide administered to a subject over the course of one day (24 hours) (daily dose), two days, one week, two weeks, three weeks or one or more months (e.g., by a single administration, or by two or more administrations). The interval between doses can be any desired amount of time.

The phrase, "half-life," refers to the time taken for the serum concentration of the fusion polypeptide to reduce by 50%, in vivo, for example due to degradation of the ligand and/or clearance or sequestration of the dual-specific ligand by natural mechanisms. The half-life of a fusion polypeptide is increased if presence in a biological matrix (blood, serum, plasma, tissue) persists, in vivo, for a longer period as compared to an appropriate control. Half life may be increased by 10%, 20%, 30%, 40%, 50% or more as compared to an appropriate control.

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences. In the case of circularly related proteins, the sequence of one of the partners needs to be appropriately split and aligned in two sections to achieve optimal alignment of the functionally equivalent residues necessary to calculate the percent identity.

Amino acid and nucleotide sequence alignments and homology, similarity or identity, as defined herein are preferably prepared and determined using the algorithm BLAST 2 Sequences, using default parameters (Tatusova, T. A. et al., FEMS Microbiol Lett, 174:187-188 (1999)). Alternatively, the BLAST algorithm (version 2.0) is employed for sequence alignment, with parameters set to default values. BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, Proc. Natl. Acad. Sci. USA 87(6):2264-8.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc. which are incorporated herein by reference) and chemical methods.

Circular Permutation of a Reference Ligand

Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

Engineered fusion proteins aim to combine the beneficial properties of two polypeptides into a single protein, however, the construction of the fusion protein comes with various challenges and risks. Often, the functional activity of the fusion protein is compromised relative that of the unmodified protein potentially due to a negative effect of the fusion partner on the integrity of the tertiary structure of the protein or on the proteins ability to bind to cognate partners (for example, due to steric hindrance) to elicit it's biological function. Furthermore, inclusion of spacers between the fusion partners can increase the potential for susceptibility to proteolysis or, in the case of therapeutic proteins, also increase the potential for immunogenicity; the longer the spacer, the greater the risk. Thus, in generating fusion proteins, preserving the structural integrity of the fusion peptide, maintaining unobstructed access for binding to the necessary cognate partners, and minimizing the length of spacer sequences are important design goals. Towards these aims, utilizing circular permutation of a ligand as described herein provides preferential locations for fusion to a second protein.

Preferential locations for the new termini are geometrically, structurally, and functionally favored (relative to the native termini) for the fusion of a desired polypeptide fusion partner, and reduce the length of the required spacer. In one embodiment, the location of the new termini is more proximal to the native position of a potential fusion partner to which the ligand may normally associate with during the stepwise formation of a cellular receptor activation complex. The orientation of the modified ligand and the fusion partner in the fusion polypeptide may be optimal to either enhance agonistic activity of the ligand to the receptor activation complex, or provide steric hindrance of the stepwise formation of the activation complex thereby providing antagonism of the activation complex.

Figure 2:
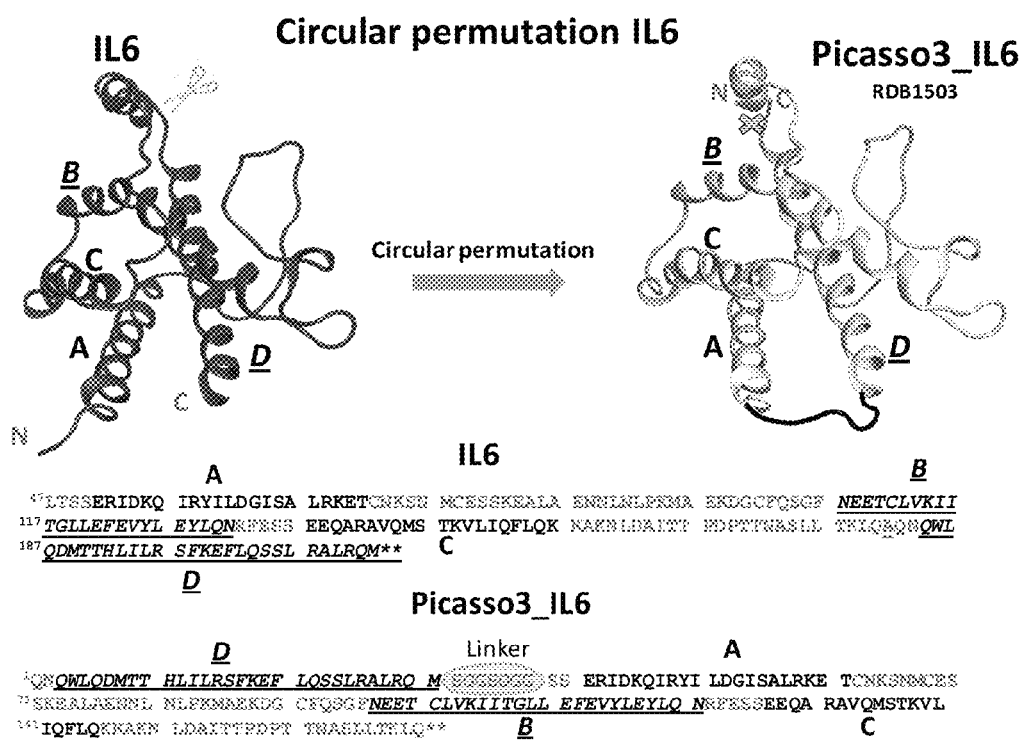
FIG. 2. Illustration of the process of circular permutation utilizing the 4-helix bundle protein, IL-6. Ribbon representation of the IL-6 crystal structure (PDB 1P9M, top left) and of modeled structure of a circularly permuted IL-6 (RDB1503, top right). N and C termini are labeled as are helicies A, B, C, D as per standard IL-6 nomenclature. The circularly permuted protein was engineered by linking the native termini and creating new termini between helicies C and D of native IL-6. The end result of the circular permutation is the relocation of the termini to the opposite face of IL-6. The amino acid sequences for IL-6 (residues 47-212 of SEQ ID NO: 3) and RDB1503 (SEQ ID NO: 1) (middle and bottom, respectively) highlight the reordered sequence. The new N-terminus of RDB1503 immediately precedes helix D. The shaded area within the ribbon representation and the protein sequence of RDB1503 highlight the linker created to connect the native IL-6 N and C termini.
Figure 3:
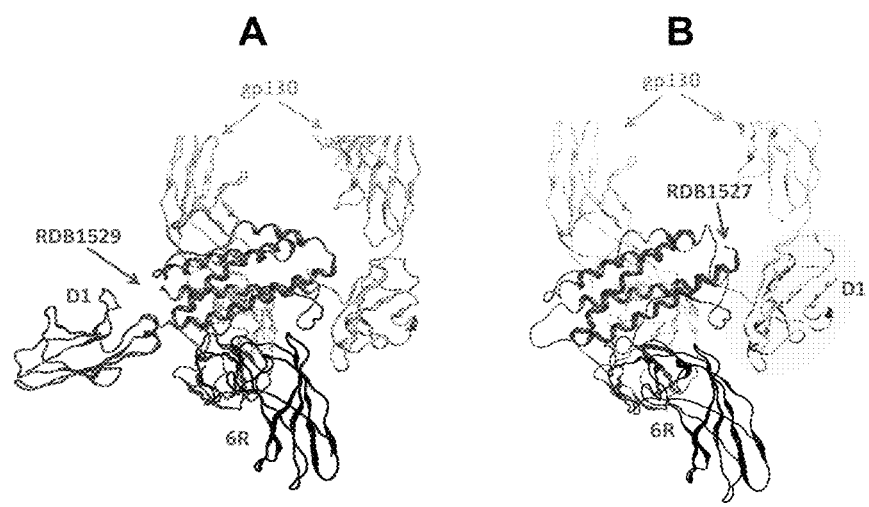
FIG. 3. Molecular model illustrating the relative orientation of the D1 (domain 1 of gp130) when fused to IL-6 (FIG. 3A) and RDB1503 (FIG. 3B), resulting in fusion proteins RDB1529 and RDB1527, respectively. The D1 domain is shaded for highlighting purposes. Portions of gp130 and IL-6Rα in the active hexameric complex are included for reference. The D1 domain of RDB1529 is pointing away from the gp130 binding interface in the hexameric active complex and is therefore predicted to be unable to effectively antagonize the signal (FIG. 3A). In contrast, the D1 domain of RDB1527 both participates in binding to IL-6Rα and occupies the space occupied by the second gp130 molecule in the hexameric complex, thus effectively antagonizing the signal (FIG. 3B).
Figure 4:
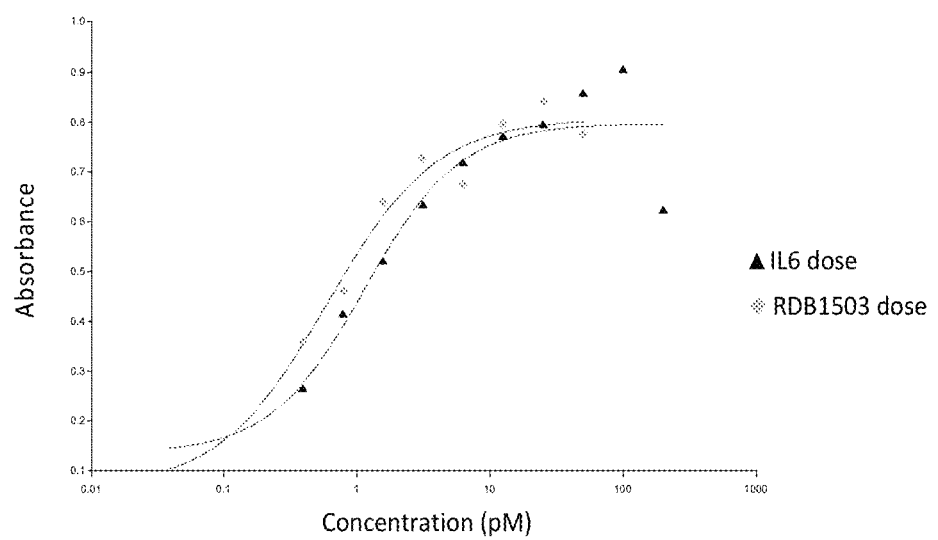
FIG. 4. Dose-response curves for IL-6 (▲) and RDB1503 (✳) in the HEK-Blue™ cell assay. The $EC_{50}$ is estimated at 1 pM and 0.6 pM, for IL-6 and RDB1503, respectively.

The process of circular permutation for IL6 is schematically illustrated in FIG. 2. The constituent amino acid residues of the native IL6 protein are numbered sequentially 47 through 212 from the amino to the carboxyl terminus.

To circularly permute IL6, recombinant constructs are engineered such that the native amino and carboxy termini of IL6 are joined by a linker sequence, and new amino and carboxy termini are engineered at amino acid residues 182 and 180, respectively. (FIG. 2). Thus, circular permutation produces a new linear protein (IL-6 (182/180), aka Picasso3) which, proceeding from the amino to the carboxy terminus, comprises the segment of the original protein corresponding to residues 182 through 212 (now 1 through 31) followed by the linker, followed by a segment of the original protein corresponding to residues 49 through 180 (now 39 through 107) (FIG. 2).

It is important to create a permutation of a native ligand that will retain the biological activity of the native form of the ligand while providing an optimal termini for fusing a desired polypeptide fusion partner. If the new termini interrupt a critical region of the native protein, activity may be lost. Similarly, if linking the original termini destroys activity, then no permutation will retain biological activity. Thus, there are two requirements for the creation of an active circularly permuted protein: 1) The termini in the native protein must be favorably located so that creation of a linkage does not destroy biological activity; and 2) There must exist an "opening site" where new termini can be formed without disrupting a region critical for protein folding and desired biological activity.

In one embodiment, the new N-terminus and C-terminus of the modified ligand do not disrupt any binding domain of the modified ligand for the target receptor.

In one embodiment, the modified ligands are as fully active as the original ligands. In one embodiment the modified ligands have enhanced activity as compared to the original ligands. In one embodiment the enhanced activity is increased binding affinity for the target receptor.

Thus, in general, good candidates for circular permutation are proteins in which the termini of the original protein are in close proximity and favorably oriented. In one embodiment, the termini of the original protein are equal to or less than 20 Å apart. Where the termini are naturally situated close together, it is expected that direct fusion of the termini to each other is possible and the introduction of a linker will have relatively little effect. However, because the linker may be of any length, close proximity of the native termini is not an absolute requirement.

In a preferred embodiment, it is desirable to use a linker sequence in the permuted protein that preserves the spacing between the amino and carboxy termini that is comparable to the spacing between the amino and carboxy termini found in the unpermuted or native molecule. In a preferred embodiment, the linker sequence will itself be between at least about one amino acid to at least about 10 amino acids. In a preferred embodiment, a small number of amino acids from either terminus may be removed (trimmed back) to bring the termini closer together. For example, in the crystal complex of IL-6 with IL-6R and gp130, the termini of the cytokine IL6 are 16 Å apart (Brevnova et al. (2003) *Science* 300:2102). Removal of the first two N-terminal residues, which are not required structurally or functionally, reduces the distance between the termini to 10.2 Å. A linkage that essentially preserves this spacing is made with the peptide sequence SGGSGGG (SEQ ID NO: 14). Similarly, a preferred linker for circularly permuted IL-1β and IL-2 are GGSGGSG and GG, respectively (SEQ ID NO: 15 and SEQ ID NO: 16, respectively).

The selection of an opening site may be determined by a number of factors. Where the three dimensional conformation of the protein is known or predicted, preferred opening sites will be located in connecting loops or regions that do not show a highly regular three-dimensional structure. Thus, it is preferred that opening sites be selected in regions of the protein that do not contain defined secondary structures such as alpha helices, β strands, and the like. Methods of identifying regions of defined secondary structure based on amino acid sequence are widely available on the World Wide Web. Furthermore, various programs are available for predicting the three-dimensional structure of proteins, recently reviewed in Nayeem et al., Protein Science, 808-24 (2006).

When retention or enhancement of the bioactivity of the native molecule is desired in the circularly permuted molecule, it is preferable that the opening site not be involved directly or indirectly in interactions with its protein partners. In one embodiment, the choice of the new opening site does not disrupt a binding domain present in the native ligand that is involved directly or indirectly in the binding affinity of the native ligand for its target receptor.

Alternatively, where the substitution of certain amino acids or the modification of the side chains of certain amino acids does not change the activity of a protein, it is expected that those amino acids are not critical to the protein's activity. Thus, amino acids that can be mutated (in vitro) or are actually modified in vivo, with little impact on the protein's activity, are potentially good candidates for opening sites. Preferred opening sites in IL-6 are between residues 131 and 135 and between residues 180 and 182. A preferred opening site in IL-1β is between residues 179 and 180, and also between residues 223 and 224. A preferred opening site in IL-2 is between residues 94 and 95.

Where the protein is a member of a family of related proteins within a species, one may infer that the highly conserved sequences are critical for biological activity, while the variable regions are not. Likewise, one may infer that highly conserved sequences of a protein which is functionally conserved across mammalian species, particularly if there is cross-species pharmacological activity, are critical for biological activity. Preferred opening sites are then selected in regions of the protein that do not show highly conserved sequence identity between various members of the protein family, either within or between species. Alternatively, preferred opening sites that are identified in a protein provide good candidate locations for opening sites in homologous proteins. Methods of determining sequence identity are well known to those of skill in the art and are described above.

One of skill in the art will recognize that other modifications may be made. Thus for example, amino acid substitutions may be made that increase the specificity or binding affinity of the ligand modified by circular permutation. Thus where there are regions of the ligand that are not themselves involved in the activity of the ligand, those regions may be eliminated or replaced with shorter segments that merely serve to maintain the correct special relationships between the ligand and the proteins that it is intended to associate with.

For a number of native ligands (e.g. growth factors, cytokines, and other proteins), the carboxy and amino termini are situated such that when fusion polypeptides are formed by joining a second polypeptide or molecule to either terminus of the native ligand, the desired downstream activity of the second polypeptide is significantly decreased or absent. Aberrant protein folding or steric hindrance is often ascribed to account for the decreased or absent activity of the second polypeptide. In other cases, fusion of a second polypeptide to either terminus of the native protein is tolerated (i.e. the functional activity of the native protein is not significantly impacted), however the orientation of the fusion polypeptide does not impart the desired activity to the fusion protein, such as in the case where the fusion polypeptide is meant to interfere (i.e. antagonize) with the formation of a signaling complex through steric interference where the location of the fusion polypeptide occupies the space that a downstream signaling molecule would occupy in the assembly of the active signaling complex.

In contrast, circular permutation of a ligand as described here provides a means by which the ligand may be altered to produce new carboxy and amino termini that permit fusion of the second molecule or polypeptide without diminishing the specificity and binding affinity of the altered ligand relative to its native form, and that also permits that the fused second molecule or polypeptide to impart, for example, superagonism or antagonism of a signaling activation complex. In one embodiment the fusion polypeptide of the invention converts a native ligand that is an agonist of a target signaling activation complex to an antagonist of the signaling activation complex. This is illustrated in the context of the cytokine, IL-6, in FIGS. 1-5.

Figure 6A:
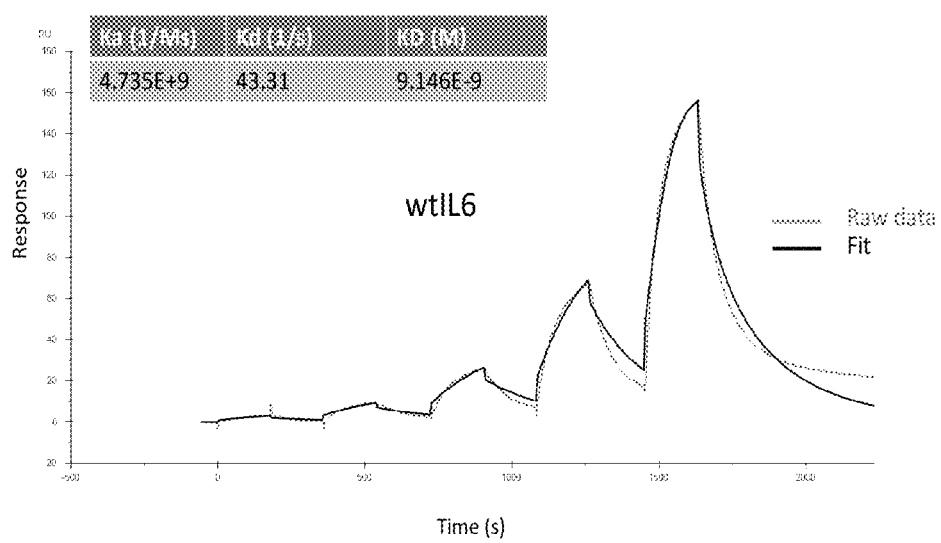
FIG. 6. Surface Plasmon Resonance (SPR) measurements of soluble IL-6Rα binding to immobilized IL-6 (FIG. 6A), RDB1529 (FIG. 6B), and RDB1527 (FIG. 6C). Sensorgrams and fitted curves are in grey and black, respectively. The kinetic parameters calculated from the data are in the inserted tables.
Figure 6B:
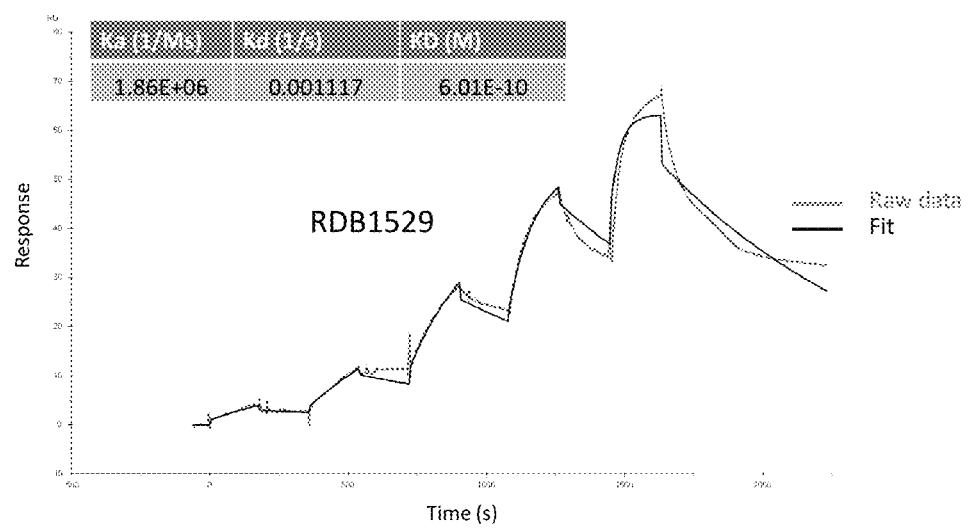
Figure 6C:
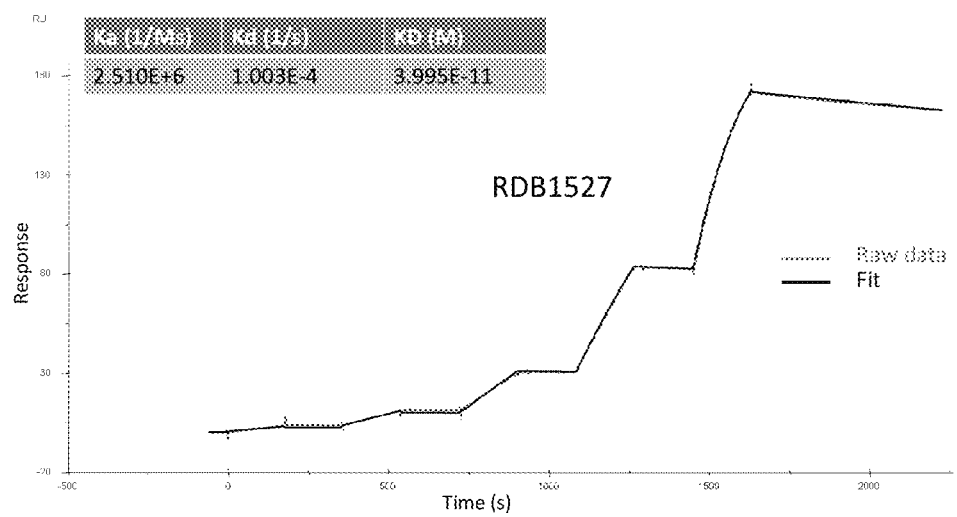

One feature of the invention is that fusion polypeptides comprised of a circularly permuted ligand fused to a fusion partner, enhance the binding affinity of the fusion polypeptide to the native ligand's native receptor relative to the binding affinity of the native (unfused, unmodified, unpermuted) ligand for its native receptor. For example, Example 3 compares the binding affinity to the IL6 receptor of, 1) a fusion polypeptide comprised of circularly permuted IL6 fused to domain one of the transmembrane signaling molecule gp130, with 2) native IL-6. The binding affinity of the fusion polypeptide is seen to be more than 200 fold greater than the binding affinity of native IL6 to the IL6 receptor (FIGS. 6A and 6C).

Fusion Polypeptides

The present invention provides for novel fusion polypeptides comprising circularly permuted (modified) ligands and at least one polypeptide fusion partner, wherein the fusion polypeptide optionally possesses specificity and binding affinity greater than the specificity and binding affinity of the native (unpermuted) ligand for its native target receptor. Additionally, the fusion polypeptide may for example, be further engineered to generate an antagonist of a pathway where the native ligand functioned as an agonist through binding a target receptor as described herein.

Figure 9:
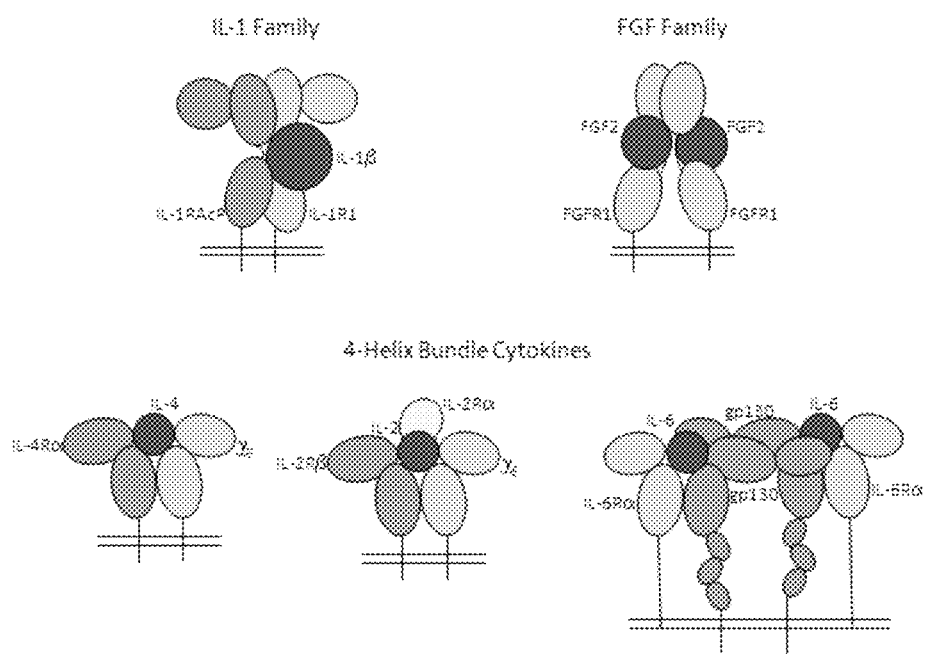
FIG. 9. Is a diagram showing representative signaling complexes for cytokines and growth factors illustrating multimeric assembly leading to activation.
Figure 10:
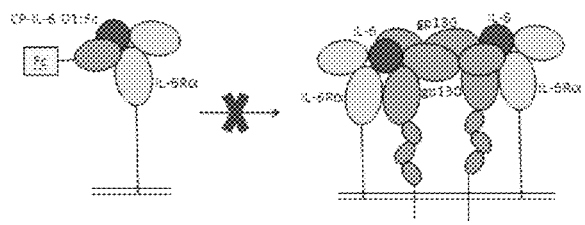
FIG. 10. Is a diagram representing the mechanism of antagonism by Picasso3_D1. Binding determinants from both IL-6 and D1 (domain of gp130) are present in the hybrid fusion protein resulting in high affinity binding to IL-6Rα. Once Picasso3_D1_Fc is bound to IL-6Rα, assembly of the signaling complex of IL-6 cannot proceed, resulting in antagonism.
Figures 11A, 11B:
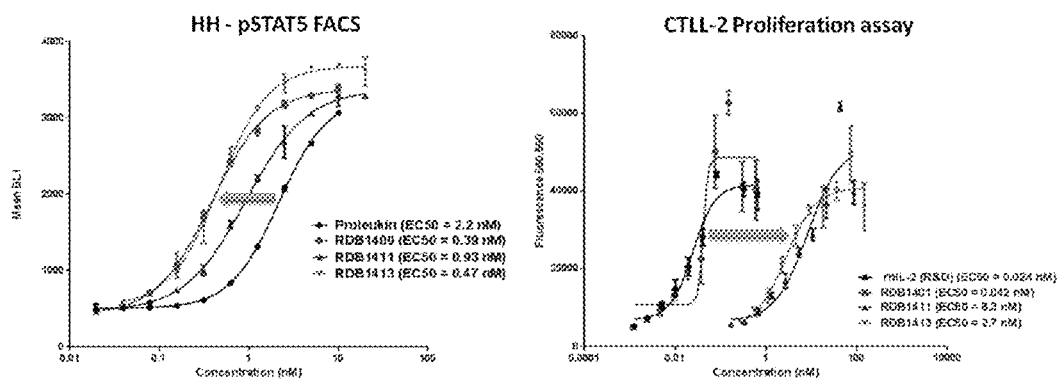
FIGS. 11A and 11B. Response of HH cells (left) and CTLL-2 cells (right) to wild-type IL-2 (Proleukin) and engineered IL-2 variants.

Many receptors bind native ligands and cluster, i.e., form dimers, trimers or multimers, upon binding their native ligands (dimeric or multimeric receptor). For example, the IL-1 family cytokines, fibroblast growth factors, and 4-helix cytokines form multimeric signaling complexes of incorporating various numbers of ligands and receptors (FIG. 9). Ligand-induced clustering (e.g., dimerization, multimerization) often leads to higher affinity complexes and initiates signal transduction. Accordingly, the fusion polypeptides of the invention can, for example, antagonize signaling by, for example, inhibiting binding of the native ligand, or inhibiting receptor clustering (e.g., dimerization, trimerization, multimerization) with or without also inhibiting native ligand binding (FIG. 10). Alternatively, the fusion polypeptides of the invention can enhance signaling by, for example, facilitating the progression of the clustering, through generation of ligands with greater affinity for target receptors or pre-association of components leading to a signaling complex. In a preferred embodiment, the fusion polypeptides of the invention can bind a monomeric ligand or receptor, or a dimeric, or multimeric complex and can inhibit or enhance one or more steps in the assembly of signaling complexes and thereby inhibit or enhance signal transduction of a cellular pathway.

For example, in the stepwise build up of higher order complexes leading to a final active complex as set forth in Scheme 1, which is representative of the pathway leading to signaling by IL-2 where IL-2 is "A", IL-2Rα is "B", IL-2Rβ is "C" and γc is "D":

Scheme 1:
A+B→AB (step 1);
AB+C→ABC (step 2);
ABC+D→ABCD (step 3);

where ABCD is the signaling complex and signaling is initiated by bringing C and D proximal to one another. (The signaling complex is illustrated in FIG. 9 and the structure of the extracellular components of the complex are in FIG. 8).

Figure 8:
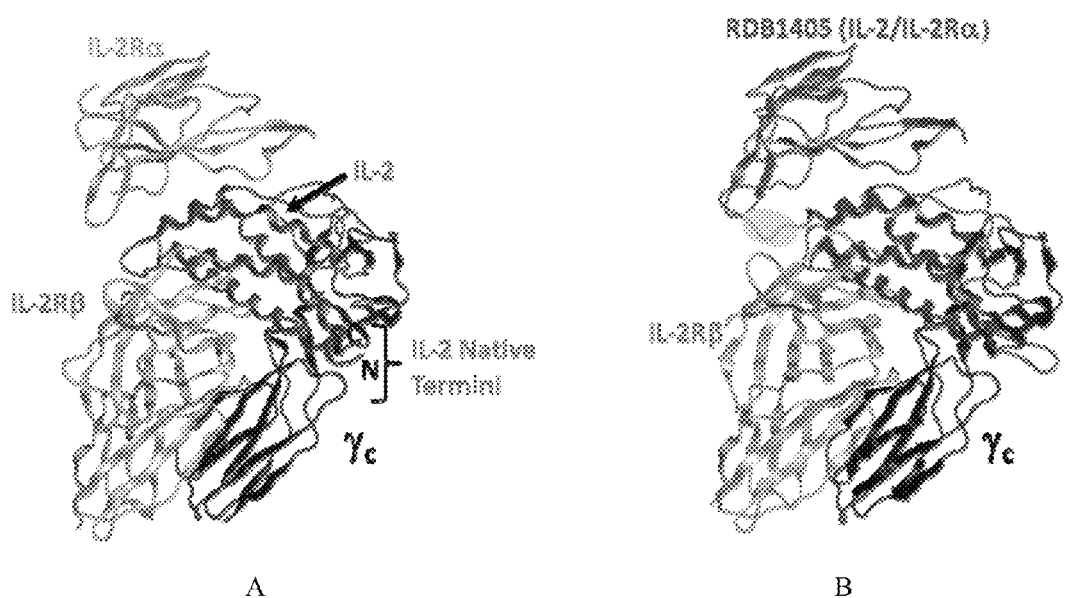
FIG. 8. Structure of the human IL2 signaling complex (PDB: 2ERJ.

A pre-assembled, single chain 'AB' would be expected to be a superagonist as it would possess a higher affinity to C than either A or B and thus facilitate assembly of ABCD at lower concentrations. In the case where the native termini of "A" are not positioned to enable the fusion protein, a fusion protein of the ligand "A" that has been modified by circular permutation in accordance with the invention to be optimally oriented to be fused with "B" enables the generation of the single chain 'AB' protein. FIG. 8 illustrates this for the case of an engineered IL-2 superagonist (RDB1405; SEQ ID NO: 12 (protein) and SEQ ID NO: 13 (DNA)). On activated T cells, IL-2 signals through the 'high affinity' quaternary complex consisting of IL-2, IL-2Rα (also termed CD25), IL-2Rβ and γc (FIG. 8A). Although IL-2 can much more weakly bind to IL-2Rβ in the absence of IL-2Rα, the binding of IL-2Rα to IL-2 stabilizes the conformation of IL-2 for presentation to IL-2Rβ with much greater affinity. γc is then recruited to the composite surface formed by the IL-2/IL-2Rβ complex. Expression of a fusion protein of native IL-2 with IL-2Rα is challenging because the IL-2 termini are at the polar opposite face to which IL-2Ra interacts, requiring a spacer to span greater than 50 angstroms and likely disrupting the ability for the fusion protein to bind (FIG. 8A, the IL-2 termini are at the bottom pointing away from IL-2Rα at the top). In fact, an IL-2/IL-2Rα fusion protein with a long spacer has recently been described, and it is incapable of promoting a signal in the absence of a protease-mediated cleavage of the linker with subsequent release of IL-2 (Puskas et al., Immunology, 133 (2), 206-220 (2011)). The termini of circularly permuted IL-2(95/94) are engineered to be on the face proximal to the binding interface with IL-2Rα, significantly reducing the length of the spacer required to generate a fusion protein that can assemble as an activated complex and may function as a super agonist (FIG. 8B). (The distance between the engineered C-terminus of the circularly permuted IL-2 and the N-terminus of IL-2Rβ is about 11 angstroms; the design fusion construct, RDB1405 contains a 6 amino acid spacer between IL-2 and IL-2Rα).

Figure 5:
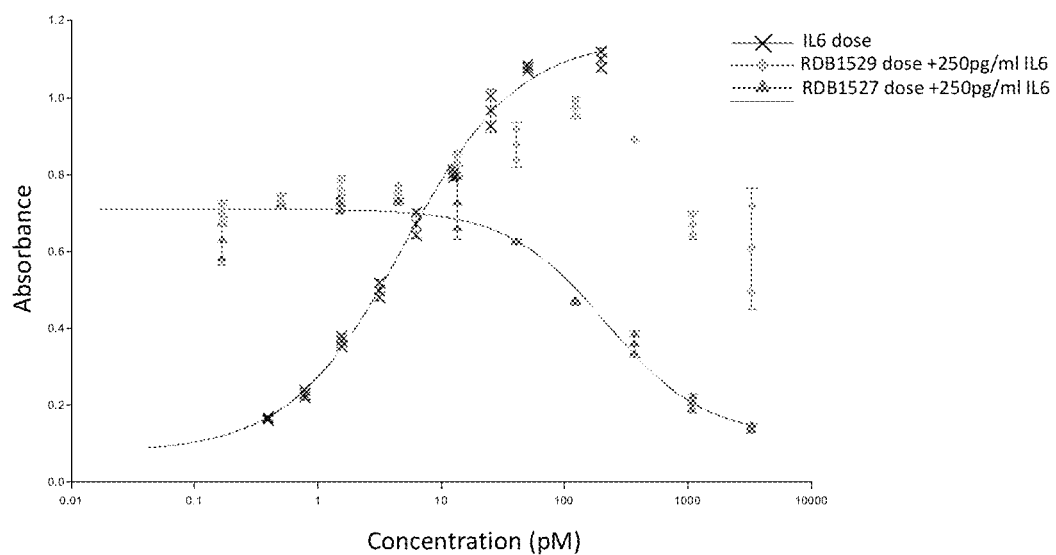
FIG. 5. Inhibition of IL6 signaling by RDB1527 in the HEK-Blue™ cell assay. Activity of IL6 (—✘—) as a function of its concentration in the absence of inhibition. Inhibition by RDB1527 (—▬—), and RDB1529 (—⁝—) were measured in the presence of 12.5 pM of IL6. All measurements were made in duplicate. The estimated value of $IC_{50}$ for RDB1527 is 0.22 nM. RDB1529 did not show robust inhibitory activity.

Alternatively, the stepwise build up of multimeric activation complexes for signal transduction offers the opportunity to create potent antagonists. In this case, the ligand is modified by circular permutation to provide an N- or C-terminus which facilitates linking a fusion partner in an orientation that sterically hinders the stepwise formation of a multimeric activation complex of a target receptor, and in some cases the fusion partner can furthermore augment the binding affinity to the target receptor, if for example, the fusion partner is a protein or domain that in itself contains binding determinants to the target receptor. This latter case is illustrated in the context of the cytokine, IL-6, in FIGS. 1-5 and 10. In this example, the fusion polypeptide comprises circularly permuted interleukin 6 (IL-6) fused to a polypeptide comprising the D1 domain of the transmembrane receptor gp130, which is a natural component of the hexameric IL-6 signaling complex. The circularly permuted ligand (RDB1503) (FIG. 2), in absence of a fusion partner, retains the identical agonistic activity as wild-type IL-6 (FIG. 4), and thus retains the necessary interactions with IL-6Rα and gp130. The hexameric signaling complex of IL-6 is composed of 2 molecules each of IL-6, IL-6Rα, and gp130 (FIG. 1). Signal is initiated through the cytoplasmic domain of the two gp130 molecules when two heterotrimers (each with one molecule each of IL-6, IL-6Rα, and gp130) come together (FIG. 1). The driving force for the final step in complex formation is the symmetrical interactions between the D1 domains of gp130 from one heterotrimer with IL-6 and IL-6Rα of the other heterotrimer. A fusion of the D1 domain of gp130 to native IL-6 orients the D1 domain away from the gp130 interface (FIG. 3A) and results in a protein (RDB1529) that does not antagonize IL-6-mediated signaling (FIG. 5). In contrast, a fusion of the D1 domain to the circularly permuted IL-6 (RDB1527) orients the D1 such that it can interact with IL-6Rα in an analogous fashion to the hexameric complex, and more importantly sterically prevent the binding of the D1 domain from a second heterotrimer (FIG. 3B), and thus is a potent antagonist of IL-6-mediated signaling (FIG. 5). As the CP_IL-6_D1 fusion protein now carries the combined IL-6Rα binding determinants of the unmodified IL-6 and the native gp130-D1 domain in a single polypeptide, the binding affinity of the fusion polypeptide is measured to be 40 pM, more than 200 fold greater than the binding affinity of native IL6 to the IL-6Rα (FIGS. 6A and 6C).

In one embodiment, the invention provides for fusion polypeptides comprising the modified ligand and a first fusion partner wherein the first fusion partner of the modified ligand is derived from all or a portion of a protein with additional binding determinants to the target receptor, for example as in the case of a protein or domain which is a component of the natural multimeric signaling complex, and the first fusion partner sterically prevents the assembly of the full signaling complex, thereby acting as an antagonist.

The ligands modified by circular permutation comprising the fusion polypeptides of the invention include soluble proteins whose binding to cell surface receptors initiate a signaling cascade or serve as natural negative regulators of a signaling cascade (eg. antagonists), including, but not limited to, cytokines, chemokines, adipokines, growth factors, hormones, soluble receptors, cytokine binding proteins (eg. IL-18 bp).

Preferred ligands and proteins modified by circular permutation comprising the fusion polypeptides of the invention include helix bundle proteins and cytokines (including, but not limited to, growth hormone, IL-2, IL-4, IL-5, IL-6, IL-10, IL-22, IL-23p19, IL-1, IL-13, IL-15, IL-12p35, IL-21, IL-30 (IL27p28), IL-34, IL-35, IL-35p35, IFN-β, IFNγ, LIF, CNTF, Oncostatin M, CLCF-1, GCSF, GM-CSF, EPO, ferritin, leptin, placental lactogen, prolactin, apolipoprotein e), b-trefoil proteins (including, but not limited to, IL-1α, IL-1β, IL-1Ra, IL18, IL-33, IL-36Ra, IL-36a, IL-36b, IL-36g, IL-37, IL-38, IL1Hy2, FGF-1, FGF-2, FGF-3, FGF-4, FGF-5, FGF-6, FGF-7, FGF-8a, FGF-8b, FGF-8e, FGF-8f, FGF-9, FGF-10, FGF-11, FGF-12, FGF-13, FGF-14, FGF-16, FGF-17, FGF-18, FGF-19, FGF-20, FGF-21, FGF-22, FGF-23), α/β (TIM) barrel proteins (including, but not limited to, triosephosphate isomerase), beta sandwich proteins (including, but not limited to, galectin-1, galectin-3, TNF-beta, seven β-propeller proteins, class 1 MHC α1α2 domain, integrin I domain, GYF domain, C1 domain, C2 domain (for example, from cPLA2, PKC, synaptotagmin), PDZ domains, C3d, C5a.

In the most preferred embodiments, the ligand modified by circular permutation comprising the fusion polypeptides of the invention is selected from IL-6, IL-2, IL-15, IL-1α, IL-1β, IL-1Rα, IL-18, FGF-19, FGF-21, FGF-23.

The ligands modified by circular permutation comprising the fusion polypeptides of the invention can have binding specificity for a receptor, or for a receptor that binds a native ligand in the following list: ApoE, Apo-SAA, BDNF, Cardiotrophin-1, EGF, EGF receptor, ENA-78, Eotaxin, Eotaxin-2, Exodus-2, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-1, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumor necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER1, HER2, HER3, and HER4.

Additional receptors that the modified ligand can have binding specificity for include the receptors in the following list, or a receptor that binds a native ligand included in the following list: EpoR, TACE recognition site, TNF BP-I, TNF BP-II, IL-1R1, IL-6R, IL-10R, IL-18R, IL-1, IL-19, IL-20, IL-21, IL-23, IL-24, IL-25, IL-27, IFN-γ, IFN-α/β, CD4, CD89, CD19, HLA-DR, CD38, CD138, CD33, CD56, CEA, and VEGF receptor.

Further receptors that the modified ligands of the fusion polypeptides of the invention can have binding specificity for include gastrin releasing peptide receptor, neurotensin receptor, adrenomedullin receptor, H2 histamine receptor, HCG receptor, MET receptor, sphingosine 1-phosphate receptor, CD126, CD213a1, and KDR, among others.

The modified ligand of the polypeptide fusion protein of the invention can have binding specificity for a receptor that dimerizes upon binding to a native ligand (a dimeric receptor), or a receptor that forms multimers, such as trimers, upon binding to a native ligand (a multimeric receptor). Many cytokine receptors and growth factor receptors, such as members of the TNF receptor superfamily (e.g., TNFR1, TNFR2) and members of the receptor tyrosine kinase family (e.g., EGFR, PDGFR, M-CSF receptor (c-Fms)) form dimers or multimers upon binding their native ligands. The TNF receptor superfamily is an art recognized group of proteins that includes TNFR1 (p55, CD120a, p60, TNF receptor superfamily member 1A, TNFRSF1A), TNFR2 (p75, p80, CD120b, TNF receptor superfamily member 1B, TNFRSF1B), CD (TNFRSF3, LTβR, TNFR2-RP, TNFR-RP, TNFCR, TNF-R-III), OX40 (TNFRSF4, ACT35, TXGP1L), CD40 (TNFRSF5, p50, Bp50), Fas (CD95, TNFRSF6, APO-1, APT1), DcR3 (TNFRSF6B), CD27 (TNFRSF7, Tp55, S152), CD30 (TNFRSF8, Ki-1, D1S166E), CD137 (TNFRSF9, 4-1BB, ILA), TRAILR-1 (TNFRSF10A, DR4, Apo2), TRAIL-R2 (TNFRSF10B, DR5, KILLER, TRICK2A, TRICKB), TRAILR3 (TNFRSF10C, DcR1, LIT, TRID), TRAILR4 (TNFRSF10D, DcR2, TRUNDD), RANK (TNFRSF11A), OPG (TNFRSF11B, OCIF, TR1), DR3 (TNFRSF12, TRAMP, WSL-1, LARD, WSL-LR, DDR3, TR3, APO-3), DR3L (TNFRSF12L), TAC1 (TNFRSF13B), BAFFR (TNFRSF13C), HVEM (TNFRSF14, ATAR, TR2, LIGHTR, HVEA), NGFR (TNFRSF16), BCMA (TNFRSF17, BCM), AITR (TNFRSF18, GITR), TNFRSF19, FLJ14993 (TNFRSF19L, RELT), DR6 (TNFRSF21), SOBa (TNFRSF22, Tnfrh2, 2810028K06Rik), and mSOB (THFRSF23, Tnfrh1). The receptor tyrosine kinase family is an art recognized group of proteins that includes EGFR (ERBB1, HER1), PDGFR, c-Fms, FGFR1, FGFR2, FGFR3, FGFR4, Insulin receptor, and Insulin-like growth factor receptors (IGF1R, IGF2R). See, Grassot et al., *Nucleic Acids Research,* 31(1):353-358 (2003).

In one embodiment, the first polypeptide fusion partner comprises all or any portion of the extracellular domains of the natural receptors or accessory proteins for growth hormone, IL-2, IL-4, IL-5, IL-6, IL-10, IL-1, IL-12, IL-13, IL-15, IL-21, IL-22, IL-23, IL-30 (IL27p28), IL-34, IL-35, IFN-β, IFNγ, LIF, CNTF, Oncostatin M, CLCF-1, GCSF, GM-CSF, EPO, placental lactogen, prolactin, apolipoprotein, IL-1α, IL-1β, IL-1Ra, IL18, IL-33, IL-36Ra, IL-36a, IL-36b, IL-36g, IL-37, IL1Hy2, FGF-1, FGF-2, FGF-3, FGF-4, FGF-5, FGF-6, FGF-7, FGF-8a, FGF-8b, FGF-8e, FGF-8f, FGF-9, FGF-10, FGF-11, FGF-12, FGF-13, FGF-14, FGF-16, FGF-17, FGF-18, FGF-19, FGF-20, FGF-21, FGF-22, FGF-23, TNF-beta.

In the most preferred embodiments, the fusion partner is the extracellular domain or a domain thereof selected from gp130 (most preferentially the D1 domain), IL-2Rα, IL-15Rα, IL-1RI, IL-1RII, IL-18Rα, IL-18Rβ, IL1RAcP, FGFR1b, FGFR1c, FGFR2b, FGFR2c, FGFR3b, FGFR3c, FGFR4, α-Klotho, and β-Klotho.

In one embodiment, the protein modified by circular permutation comprising the fusion polypeptides of the invention and the fusion partner may originate from the same original protein such that the fusion generates a single chain "homodimer".

In one embodiment, the fusion partner to the circularly permuted polypeptide may also require circular permutation to enable the fusion. Thus both partners of the fusion protein of the invention may be circularly permuted, if necessary.

In one embodiment the polypeptide fusion partner provides other novel or improved/enhanced functions or behavior to the fusion polypeptide. In addition to, or alternatively, a second fusion partner may be added to the fusion polypeptide of the invention to provide other novel and improved/enhanced functions or behavior to the fusion polypeptide of the invention. For example, the fusion partners may provide extended half life to the fusion polypeptide of the invention. Addition of fusion partners to extend in vivo half-life is particularly useful when the fusion polypeptide of the invention is of a size that is rapidly cleared from the body, which can limit clinical use.

A polypeptide of the invention can be modified such that it has a larger hydrodynamic size by for example, coupling to polymers or carbohydrates (such as polyethyleneglycol (PEG), colominic acid, or hydroxyethyl starch), incorporation of N-glycosylation sites, or through recombinant PEG mimetics produced through fusion of a long, flexible polypeptide sequence, such as those described in U.S. 2010/0239554 A1, Hydrodynamic size of a polypeptide fusion protein of the invention may be determined using methods which are well known in the art. For example, gel filtration chromatography may be used to determine the hydrodynamic size. Suitable gel filtration matrices for determining the hydrodynamic sizes of ligands, such as cross-linked agarose matrices, are well known and readily available.

In one preferred embodiment, a fusion polypeptide of the invention is designed to incorporate a mucin-domain polypeptide as is described in U.S. Ser. No. 61/657,264 entitled "Fusion Polypeptides Comprising an Active Protein Linked to a Mucin-Domain Polypeptide" filed on even date herewith, and incorporated by reference herein in its entirety.

In one embodiment, a fusion polypeptide of the invention can be fused to proteins, protein domains, or peptides that that enhance serum half-life through FcRn-mediated recycling, including immunoglobulins, the Fc domain of immunoglobulins (most notably IgG1 and IgG2), serum albumin, serum albumin domains (most notably DIII), peptides with binding affinity to FcRn, or proteins or peptides with binding affinity to immunoglobulins or serum albumin (such as nanobodies).

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

In one embodiment, a fusion polypeptide of the invention can be fused to proteins, protein domains, or peptides that that target (i.e. have affinity for) specific organs, tissues, cells, or physiological matrices (such as collagen), carbohydrates, or lipids as a means for localizing, distributing, or retaining the fusion polypeptide of the invention in a particular region of the body.

Additional sequences also can be included as part of the fusion polypeptide such as affinity tag sequences that can be provided to facilitate the purification or isolation of the fusion polypeptide such as those known in the art. Stability sequences can also be added to the fusion polypeptide to protect the molecule from degradation (e.g., by a protease). Suitable stability sequences include, but are not limited to, glycine molecules incorporated after the initiation methionine (e.g., MG (SEQ ID NO: 17), or MGG (SEQ ID NO: 18) to protect the fusion molecule from ubiquitination; two prolines incorporated at the C-terminus (conferring protection against carboxypeptidase action), and the like.

In order to test the biological activity, binding specificity and binding affinity of a fusion polypeptide of the invention, an appropriate biological assay may be used. Assays for biological activities of various kinds are well known to those of skill in the art. The particular assay depends on the particular activity of the molecule.

Preparation of Circularly Permuted Proteins

Circularly permuted proteins may be made by a number of means known to those of skill in the art. These include chemical synthesis, modification of existing proteins, and expression of circularly permuted proteins using recombinant DNA methodology. Where the protein is relatively short (i.e., less than about 50 amino acids) the circularly permuted protein may be synthesized using standard chemical peptide synthesis techniques. If the linker is a peptide, it may be incorporated during the synthesis. If the linker is not a peptide, it may be coupled to the peptide after synthesis. Solid phase synthesis in which the C-terminal amino acid of the sequence is attached to an insoluble support followed by sequential addition of the remaining amino acids in the sequence is the preferred method for the chemical synthesis of the circularly permuted ligands and fusion proteins of this invention. Techniques for solid phase, synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963), and Stewart et al., Solid Phase Peptide Synthesis, 2nd ed. Pierce Chem. Co., Rockford, Ill. (1984) which are incorporated herein by reference.

Alternatively, the circularly permuted protein may be made by chemically modifying a native protein. Generally, this requires reacting the native protein in the presence of the linker to form covalent bonds between the linker and the carboxyl and amino termini of the protein, thus forming a circular protein. New termini are then formed by opening the peptide bond joining amino acids at another location. This may be accomplished chemically or enzymatically using, for example, a peptidase.

In a preferred embodiment, the circularly permuted protein, or fusion polypeptides comprising the circularly permuted protein fused to at least one fusion partner, will be synthesized using recombinant DNA methodology. Generally this involves creating a DNA sequence that encodes the circularly permuted ligand (or entire fusion polypeptide containing the circularly permuted ligand and fusion partner), placing the DNA in an expression vector under the control of a particular promoter, expressing the protein in a host, isolating the expressed protein and, if required, renaturing the protein.

DNA encoding the circularly permuted ligand may be produced by gene synthesis, or by using DNA amplification methods, for example polymerase chain reaction (PCR) and reverse transcription polymerase chain reaction (RT-PCR). DNA encoding a signal sequence such that the properly processed circularly permuted fusion protein is secreted from the cell can optionally be added.

One of skill will appreciate that the circularly permuted ligand and the other molecule comprising the fusion polypeptides of the invention may be joined together in any order. Thus, the second molecule is preferably joined to either the amino (N-terminal fusion) or carboxy (C-terminal fusion) terminus of the circularly permuted ligand.

The circularly permuted ligands and their fusion proteins may be expressed in a variety of host cells, including E. coli, other bacterial hosts, yeast, and various higher eukaryotic cells such as the COS, CHO and HeLa cells lines and myeloma cell lines. The recombinant protein gene will be operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred (transfected) into the chosen host cell by well-known methods such as calcium chloride transformation for E. coli and calcium phosphate treatment, electroporation, lipofectamine treatment, or PEI treatment for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity chromatography, column chromatography with ionic or hydrophobic resins, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)). Substantially pure compositions of at least about 90 to 95% purity are preferred, and 98 to 99% or higher purity are most preferred for pharmaceutical uses. Once purified, the polypeptides may be tested in preclinical models, tested clinically, or used therapeutically.

One of skill would recognize that modifications can be made to the circularized protein sequence without diminishing its biological activity. Some modifications may be made to facilitate the cloning, expression, or incorporation of the circularly permuted ligand into a fusion protein. Such modifications are well known to those of skill in the art and include, addition of residues for example, a methionine added at the amino terminus to provide an initiation site, or additional amino acids placed on either terminus to protect the protein from exopeptidases. For example, circularly permuted IL6 may optionally have an additional methionine (Met) codon at the amino terminus to provide an initiation site for translation.

One of skill will recognize that other modifications may be made. Thus, for example, amino acid substitutions may be made that increase specificity or binding affinity of the circularly permuted protein, etc. Alternatively, non-essential regions of the molecule may be shortened or eliminated entirely. Thus, where there are regions of the molecule that are not themselves involved in the activity of the molecule, they may be eliminated or replaced with shorter segments that merely serve to maintain the correct spatial relationships between the active components of the molecule.

The two proteins may be fused together directly or joined by means of a peptide spacer. The peptide spacer may range from about 1 to 40 residues in length. In a preferred embodiment, the peptide spacer is 20 Å or less in length.

Generally, the spacer has no biological activity itself and functions only to link and provide some distance between the two active proteins comprising the fusion protein. However, one of skill will recognize that the residues of the spacer may be chosen to optimize a property of the fusion protein. For example, a spacer containing polar or charged residues in the spacer may enhance solubility in aqueous solutions. Similarly, the spacer residues may be chosen for their effect on the folding of the fusion protein.

It is understood that the invention includes the above-described nucleic acids encoding the fusion polypeptides of the inventions such as recombinant nucleic acids produced by recombinant DNA methodology, as well as expression vectors comprising the nucleic acids of the invention and host cells comprising the vectors of the invention.

Therapeutic Uses

The fusion polypeptides of the invention compositions described herein are particularly well suited as therapeutic agents targeting cells of interest in vivo (i.e., target cells) since they exhibit, among other properties, higher binding affinities for native receptors than native ligands, and super agonist and antagonistic activities. Thus, the compositions and pharmaceutical compositions containing the present fusion polypeptides can be administered to a patient in need for therapeutic treatments. In therapeutic applications, fusion polypeptides of the invention comprising circularly permuted ligands, and various compositions containing these molecules are administered to a patient suffering from a disease or disorder in a therapeutically effective amount.

The invention provides compositions comprising the fusion polypeptides of the invention and a pharmaceutically acceptable carrier, diluent or excipient, and therapeutic and diagnostic methods that employ the ligands or compositions of the invention.

Therapeutic and prophylactic uses of ligands of the invention involve the administration of ligands according to the invention to a recipient mammal, such as a human. The fusion polypeptides of the invention preferably bind to targets with high affinity and/or avidity. Substantially pure ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the fusion polypeptides of the invention may be used diagnostically or therapeutically (including extracorporeally)

or in developing and performing assay procedures, immunofluorescent stainings and the like.

For example, the fusion polypeptides of the present invention will typically find use in preventing, suppressing or treating disease states. For example, fusion polypeptides can be administered to treat, suppress or prevent a disease or disorder caused by receptor activity, or characterized by expression or overexpression of receptor, such as chronic inflammation or chronic inflammatory diseases, cardiovascular diseases, metabolic diseases (e.g., obesity, Type II diabetes, metabolic syndrome), respiratory diseases (e.g., asthma, COPD), ophthalmic diseases (e.g., AMD, glaucoma), hematopoietic disorders, immunosuppression, organ transplant rejection, graft versus host disease, bone and cartilage diseases (osteoporosis, osteoarthritis), allergic hypersensitivity, cancer, bacterial or viral infection, autoimmune disorders (which include, but are not limited to, Type I diabetes, asthma, multiple sclerosis, rheumatoid arthritis, juvenile rheumatoid arthritis, psoriatic arthritis, spondylarthropathy (e.g., ankylosing spondylitis), autoinflammatory disorders, systemic lupus erythematosus, inflammatory bowel disease (e.g., Crohn's disease, ulcerative colitis), myasthenia gravis and Behcet's syndrome), psoriasis, endometriosis, and abdominal adhesions (e.g., post abdominal surgery).

One preferred application is, through the use of the circularly permuted IL-2 fused to IL-2Rα generating an IL-2 super agonist), the treatment of cancer, or of autoimmune conditions such as graft-versus-host disease, organ transplant rejection.

Another preferred application is, through the use of a circularly permuted IL-6 fused to the D1 domain of gp130 (generating a very potent IL-6 antagonist), the treatment of chronic inflammatory diseases, autoimmune diseases (including, but not limited to, rheumatoid arthritis, psoriasis, psoriatic arthritis, juvenile rheumatoid arthritis, Crohn's disease, inflammatory bowel syndrome), cancer (including multiple myeloma), and Castleman's disease. As described in Examples 2 and 3, the circularly permuted ligand-gp130 fusion protein of the present invention (RDB1527) shows greater specific binding affinity to the native IL6 receptor (FIG. 6A vs. 6C) and target cell inhibition (FIG. 5), as compared to native ligands. The increased binding affinity and growth inhibition of circularly permuted IL6-gp130 fusion polypeptides may allow the these fusion proteins to be administered at lower dosages as compared to other inhibitors of IL6 signaling, while achieving the same therapeutic efficacy. Alternatively, administration at the same dosages results in prolonged therapeutic efficacy as the fusion proteins must be cleared from the circulation to a lower concentration before they cease to show significant efficacy. In addition, the increased therapeutic efficacy is not accompanied by an increase in undesired side effects due to non-specific binding and cytotoxicity.

Another preferred application is, through the use of a circularly permuted IL-1 fused to a domain of either IL-1RI, IL-1RII, or IL-1RAcP (generating a very potent IL-1 antagonist), the treatment of autoinflammatory diseases, Type I diabetes, chronic inflammatory diseases, autoimmune diseases (including, but not limited to, rheumatoid arthritis, psoriasis, psoriatic arthritis, juvenile rheumatoid arthritis, Crohn's disease, inflammatory bowel syndrome), cancer, gout, and osteoarthritis.

Another preferred application is, through the use of the circularly permuted IL-15 fused to IL-15α (generating an IL-15 super agonist), the treatment of cancer, of autoimmune conditions such as graft-versus-host disease, organ transplant rejection, or of infection.

The circularly permuted ligand portion of the fusion polypeptide is chosen according to the intended use. Proteins that may serve as targets for the circularly permuted ligands include but are not limited to signaling molecules such as growth factors or biologically active fragments or mutants thereof. For example, the growth factor can be a cytokine (e.g., an interleukin or chemokine). While one of ordinary skill in the art can readily determine whether a molecule is a signaling molecule (i.e., whether it is produced and secreted by a first cell type and exerts an effect on itself or (autocrine) or on a second cell type (paracrine), usually by specifically binding a receptor), various particular signaling molecules may be properly placed in two or more categories. For example, IL-1 may be properly referred to as a cytokine or interleukin and erythropoietin may be properly referred to as a growth factor or a hormone; etc.

An cytokine includes but is not limited to, IL-1α, IL-1β, IL-1Rα, IL-2, IL-3, IL-4, IL-5, IL-6, IL-7, IL-8, IL-9, IL-10, IL-1, IL-12, IL-12p35, IL-13, IL-15, IL-17 family members, IL18, IL-21, IL-22, IL-23, IL-23p19, IL-30 (IL27p28), IL-33, IL-34, IL-35, IL-35P35, IL-36Rα, IL-36a, IL-36b, IL-36g, IL-37, IL-38, LIF, CNTF, Oncostatin M, CLCF-1, GCSF, GM-CSF, ferritin, placental lactogen, apolipoprotein e, interferon-alpha (IFNα), interferon-beta (IFNβ), or interferon-gamma (IFNγ). A chemokine can be a member of the α subfamily and/or can bind a CXCR1, CXCR2, CXCR3, CXCR4, or CXCR5 receptor; it can be a member of the β subfamily and/or can bind a CCR1, CCR2, CCR3, CCR4, CCR5, CCR6, CCR7, CCR8, CCR9, CCR10, or CCR11 molecule. A chemokine can also be lymphotactin or another chemokine that binds a XCR1 receptor; a chemokine can also be fractalkine or can bind a $CX_3CR1$ receptor. For example, the chemokine can be CCL7, CCL23, CCL27, CCL28, CXCL12, CXCL14, or CXCL15.

Growth factors include but are not limited to members of the tumor necrosis factor (TNF) family, members of the nerve growth factor (NGF) family, members of the transforming growth factor (TGF) family, members of the GDF family, members of the BMP family, members of the fibroblast growth factor (FGF) family (including FGF-1, FGF-2, FGF-3, FGF-4, FGF-5, FGF-6, FGF-7, FGF-8a, FGF-8b, FGF-8e, FGF-8f, FGF-9, FGF-10, FGF-11, FGF-12, FGF-13, FGF-14, FGF-16, FGF-17, FGF-18, FGF-19, FGF-20, FGF-21, FGF-22, FGF-23, members of the insulin-like growth factor (IGF) family, members of the epidermal growth factor (EGF) family, or members of the platelet-derived growth factor (PDGF) family. For example, the growth factor can be TNF, EGF, TGFα, TGFβ, FGF, NGF, erythropoietin, IGF-1, or IGF-2.

A hormone can be a hormone produced by the adrenal gland, parathyroid gland, pituitary gland, or thyroid gland; it can also be produced by the hypothalamus, the ovary, the testicle, the pancreas, the pineal body, or the thymus. For example, the hormone can be a thyroid-stimulating hormone, a follicle-stimulating hormone, a leuteinizing hormone, prolactin, growth hormone, adrenocorticotropic hormone, antidiuretic hormone, oxytocin, thyrotropin-releasing hormone, gonadotropin-releasing hormone, growth hormone-releasing hormone, corticotropin-releasing hormone, somatostatin, dopamine, melatonin, thyroxine, calcitonin, parathyroid hormone, a glucocorticoid, a mineralocorticoid, an androgen, adrenaline, an estrogen, progesterone, human chorionic gonadotropin, insulin, glucagons, somatostatin, erythropoietin, calcitriol, atrial-natriuretic peptide, gastrin, secretin, cholecystokinin, somatostatin, neuropeptide Y, ghrelin, $PYY_{3-36}$, insulin-like growth factor-1, angiotensinogen, thrombopoietin, or leptin.

Neurotransmitters include acetylcholine, dopamine, norepinephrine, serotonin, histamine, or epinephrine. The neurotransmitter can also be a neuroactive peptide (e.g., bradykinin, cholecystokinin, gastrin, secretin, oxytocin, a sleep peptide, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, leuteinizing hormone, calcitonin, or vasoactive intestinal peptide). Suitable co-stimulatory molecules include B7-1 and B7-2.

Pharmaceutical Compositions

The present invention provides pharmaceutical compositions comprising fusion proteins of the invention. In one embodiment, the pharmaceutical composition comprises the fusion protein and at least one pharmaceutically acceptable carrier. Fusion proteins of the present invention can be formulated according to known methods to prepare pharmaceutically useful compositions, whereby the polypeptide is combined with a pharmaceutically acceptable carrier vehicle, such as aqueous solutions or buffers, pharmaceutically acceptable suspensions and emulsions. Examples of non-aqueous solvents include propyl ethylene glycol, polyethylene glycol and vegetable oils. Therapeutic formulations are prepared for storage by mixing the active ingredient having the desired degree of purity with optional physiologically acceptable carriers, excipients or stabilizers, as described in Remington's Pharmaceutical Sciences 16th edition, Osol, A. Ed. (1980), in the form of lyophilized formulations or aqueous solutions.

More particularly, the present pharmaceutical compositions may be administered for therapy by any suitable route including subcutaneous, subcutaneous or intrathecally by infusion pump, intramuscular, intravenous, intradermal, intravitreal, nasal, and pulmonary. It will also be appreciated that the preferred route will vary with the therapeutic agent, condition and age of the recipient, and the disease being treated.

In one embodiment, the pharmaceutical composition is administered subcutaneously. In this embodiment, the composition may be supplied as a lyophilized powder to be reconstituted prior to administration. The composition may also be supplied in a liquid form, which can be administered directly to a patient. In one embodiment, the composition is supplied as a liquid in a pre-filled syringe such that a patient can easily self-administer the composition.

In another embodiment, the compositions of the present invention are encapsulated in liposomes, which have demonstrated utility in delivering beneficial active agents in a controlled manner over prolonged periods of time. Liposomes are closed bilayer membranes containing an entrapped aqueous volume. Liposomes may also be unilamellar vesicles possessing a single membrane bilayer or multilamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. In one embodiment, the liposome may be coated with a flexible water soluble polymer that avoids uptake by the organs of the mononuclear phagocyte system, primarily the liver and spleen. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilic peptide sequences as described in U.S. Pat. Nos. 6,316,024; 6,126,966; 6,056,973 and 6,043,094, the contents of which are incorporated by reference in their entirety.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phasphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3 [N—(N',N'-dimethylaminoethane) carbamoly] cholesterol (DC-Chol); or dimethyldioctadecylammonium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

For liquid formulations, a desired property is that the formulation be supplied in a form that can pass through a 25, 28, 30, 31, 32 gauge needle for intravenous, intramuscular, intraarticular, or subcutaneous administration.

In other embodiments, the composition may be delivered via intranasal to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs. Preparation of a pharmaceutical composition for delivery in a subdermally implantable device can be performed using methods known in the art, such as those described in, e.g., U.S. Pat. Nos. 3,992,518; 5,660,848; and 5,756,115.

A typical pharmaceutical composition for parenteral administration would be about 0.1 to 3 mg/kg per patient per day. Methods for preparing parenterally administrable compositions will be known or apparent to those skilled in the art and are described in more detail in such publications as Remington's Pharmaceutical Science, 15th ed., Mack Publishing Company, Easton, Pa. (1980).

Single or multiple administrations of the compositions may be administered depending on the dosage and frequency as required and tolerated by the patient. In any event, the composition should provide a sufficient quantity of the proteins of this invention to effectively treat the patient.

EXAMPLES

The following examples are offered by way of illustration and are not to be construed as limiting the invention as claimed in any way.

Example 1

Design, Preparation, Expression, and Purification of Picasso Fusion Constructs

1. Design of Circularly Permutated IL-6 and Fusion to Domain D1 of gp130 Receptor The crystal structure of the hexameric IL-6 signaling complex (1P9M.pdb; FIG. 1) was utilized to design a circularly permutated variant of human IL6, named picasso3 (FIG. 2; RDB1503; SEQ ID NO: 1 (protein) and SEQ ID NO: 2 (nucleic acid)), such that the engineered C-terminus can be fused to the N-terminus of the D1 domain of gp130 in the complex through a short spacer. Briefly, the engineered N and C termini in picasso3 correspond to residues 182 and 180 in wild-type IL-6 (SEQ ID NO: 3), and the native IL-6 termini were joined through a 7 amino acid linker. The D1 domain of gp130 was chosen as the fusion partner such that not only would it interfere sterically with hexamer formation, but also enhance the binding affinity to IL-6R through native interactions present in the complex (FIG. 3B). The engineered C-terminus of picasso3 was fused to the D1 domain through a two amino acid spacer to form RDB1527 (FIG. 3B; SEQ ID NO: 4 (protein) and SEQ ID NO: 5 (nucleic acid)). As a control an analogous fusion protein consisting of native IL6 fused to D1 (RDB1529) was designed (FIG. 3A; SEQ ID NO: 6 (protein) and SEQ ID NO: 7 (nucleic acid)).

2. Gene Synthesis

Synthesis of the genes for expression of the designed constructs was carried out using standard methods.

3. Subcloning of the Synthesized Gene into a Mammalian Expression Vector

A) Preparation of the Expression Vector pcDNA™ (Invitrogen).

5 μg of pcDNA was digested with BamHI and HindIII for two hours at 37° C. The digest was treated with calf alkaline phosphatase to remove the 5' phosphate, thus preventing religation of vector on itself. Buffer was exchange to remove salts from calf alkaline phosphatase reaction. Qiagen's PCR cleanup kit was used following the manufacturer's suggested protocol. The DNA was eluted in 30 μl of H20.

B) Preparation of the Gene of Interest.

The gene of interest was digested with BamHI and HindIII for two hours 37° C. The digestion reaction was run on an E-Gel® CloneWell™ apparatus (Invitrogen) using 0.8% SYBR Green. The fragment corresponding to the gene of interest was isolated from the second row of wells on the gel.

C) Ligation Reaction of the Gene to pcDNA.

The prepared pcDNA (step A) was mixed with the DNA from step B in the presence of T4 ligase and incubated at room temperature for 30 minutes. Following the ligation, the products were transformed into TOP 10 cells (Invitrogen; chemically competent strain of *E. coli*) and the correct clone was picked and stored as a glycerol stock at the −80° C.

4. Expression of RDB1503, RDB1527, and RDB1529

All the proteins were expressed in CHO cells using FreeStyle™ Max Reagent (Invitrogen) following the manufacturer's protocol. Briefly, a day prior to transfection the cells were seeded at $0.5\times10^6$ cells/mL and on the day of transfection they were adjusted to $1\times10^6$ cells/mL as recommended by manufacturer. For a 1 liter transfection, two tubes (A and B) of media (OptiPRO™, Invitrogen) were prepared containing about 19 ml, 1 mg of DNA was added to tube A and 1 ml of FreeStyle™ Max reagent was added to tube B. Immediately the contents of both tubes were mixed and incubated at room temperature for 15 minutes. After the incubation period the mixture was added slowly to the 1 liter of CHO cells. After transfection the cells were left for 6-to-7 days and then the supernatant was collected.

5. Purification of RDB1527 and RDB1529

The expressed protein in the supernatant was captured on a protein A column to bind the Fc portion of the fusion protein. After binding the protein, the column was washed with up to 5 column volume of PBS. The protein was eluted from the column by lowering the pH of the running buffer and directly neutralized with Tris buffer pH=7. The purified protein was then dialyzed overnight against PBS.

Example 2

In Vitro Activity of Circularly Permutated IL6 Fusion Proteins

HEK-Blue™ IL-6 cells (Invivogen) are human embryonic kidney cells specifically designed to detect bioactive IL-6 in vitro by monitoring the IL-6-induced expression of a STAT3-inducible secreted embryonic alkaline phosphatase (SEAP) reporter gene. SEAP can be readily monitored when using the SEAP detection medium QUANTI-Blue™ (Invivogen). The human cell line and detection medium were used to test the ability of the circularly permutated IL6 and IL6 fusion proteins constructs RDB1503, RDB1527 and RDB1529 to agonize or antagonize the IL-6-induced SEAP.

100 μL of media containing HEK-Blue™ IL-6 cells were plated into 96-well microtiter plates to a final concentration of 50,000 cells/well. To measure agonist activity, IL6 and RDB1503 were prepared at initial concentration of 200 μM then serially diluted and added in duplicate test samples to the HEK-Blue™ IL-6 cells. To measure antagonist potency, RDB1527 and RDB1529 were prepared at an initial concentration of 3.3 nM then serially diluted and added in duplicate test samples to the HEK-Blue™ IL-6 cells in the presence of a constant concentration of IL6 of 12.5 pM. The samples were incubated at 37° C., 5% CO2 from 20-24 hours, then 40 μL of each sample transferred to a new 96 well plate containing 160 μL of QUANTI-Blue™ in each well, and incubated at 37° C., 5% CO2. Absorbance readings were taken at 630 nm after 3 hours of incubation.

Circularly permuted IL-6 (RDB1503) demonstrated agonist activity with a comparable $EC_{50}$ to that of IL-6 (FIG. 4). RDB1527 (CP_IL-6_D1_Fc) was able to inhibit IL-6-induced SEAP expression in a dose-dependent fashion with an $IC_{50}$ value of 0.22 nM (FIG. 5). In contrast, RDB1529 (unmodified IL-6_D1_Fc) showed no antagonist effect (FIG. 5).

The following conclusions were drawn: 1) Circular permutation of IL-6 results in no loss in binding affinity; 2) fusion of the D1 domain of gp130 to the C-terminus of wild type IL-6 does not convert IL-6 to a potent antagonist, whereas fusion of the D1 domain of gp130 to the C-terminus of the circularly permuted IL-6 results in potent antagonism of IL-6 mediated signaling.

Example 3

Kinetics Measurements of wtIL6, RDB1527 and RDB1529

Wild type IL6-Fc (wtIL6), RDB1527 and RDB1529 were immobilized on a Biacore™ sensor chip using the human antibody capture kit (GE Healthcare) as per manufacturer's protocol. IL-6R was passed over the surface of the chip in a stepwise model. IL-6R was prepared in 5 concentrations; 3.0 nM, 1.0 nM, 0.33 nM, 0.11 nM, and 0.03 nM. In the First cycle the 0.03 nM concentration of IL-6R was flowed over the bound ligand on the surface of the chip for 180 seconds, after which a blank solution was passed over the surface to allow the IL-6R to dissociate. The same procedure was repeated for an additional four times using an increasing concentration from 0.03 to 3 nM of 6R. The resulting sensorgrams were analyzed with the native instrument software to calculate the binding affinities of the constructs. The binding affinity of RDB1527 to IL-6R was calculated to be 40 pM (FIG. 6C), representing an increase of over 200-fold when compared to the affinity of the control wtIL6 (9 nM, FIG. 6A). The sensorgram for RDB1529 (FIG. 6B) resulted in a poor fit, and thus the calculated binding affinity is not reliable. This may be due to mixed binding between IL-6 and IL-6R and independently D1 and IL-6R.

Based upon the results it was concluded that the binding affinity of RDB1527 to IL-6R is 40 pM, or greater than 200-fold higher than that of wtIL6. This data, in combination with the potent antagonist activity, strongly suggests that the binding determinants on IL-6 and on D1 are simultaneously binding to IL-6R, and preventing association of the signaling complex, as designed.

Example 4

Design of Circularly Permutated IL1β Fused to Domains D1-D2 of IL-1RI (RDB1538)

Figure 7:
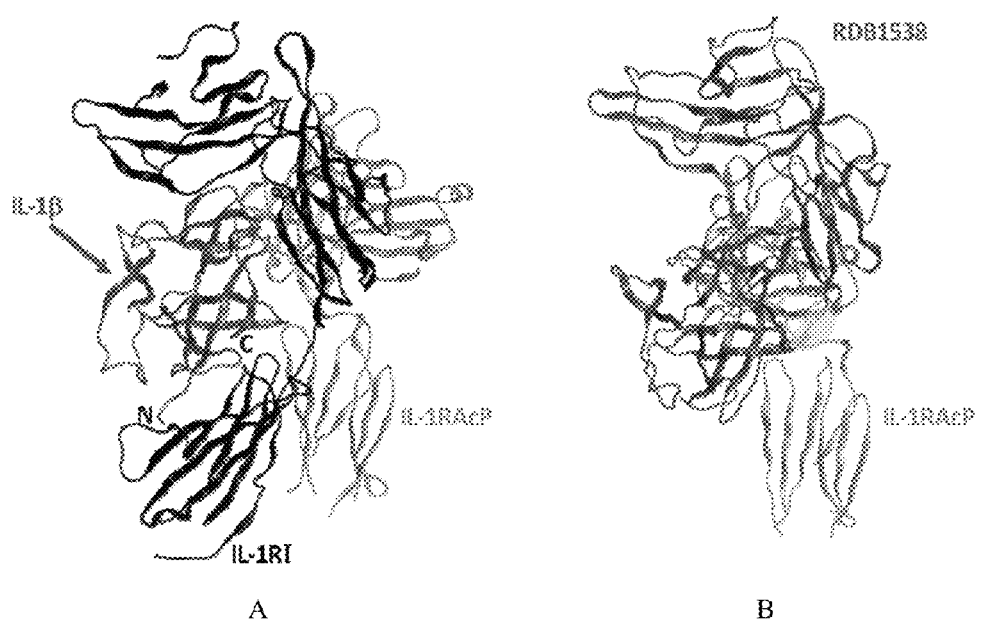
FIG. 7. Structure of the human IL-1β signaling complex (PDB: 4DEP.

The crystal structure of the heterotrimeric IL-1β signaling complex (4DEP.pdb; FIG. 7A) was utilized to design a circularly permutated variant of IL-1β (RDB1515; SEQ ID NO: 8 (protein) and SEQ ID NO: 9 (nucleic acid)), such that the engineered N terminus can be fused to the C-terminus of the D1-D2 domain of IL-1RI through a short spacer. Briefly, the engineered N and C termini correspond to residues 224 and 223, respectively, in wild-type IL-1β, and the native IL-1β termini were joined through a 7 amino acid linker. The newly created N-terminus was fused to domain D1-D2 of RI with a 5 amino acid spacer and a FLAG tag was added to the N-terminus of RI, resulting in RDB1538 (FIG. 7B; SEQ ID NO: 10 (protein) and SEQ ID NO: 11 (nucleic acid)). The resulting fusion protein is designed to be an antagonist of IL-1β-mediated signaling by binding to IL-1RAcP and preventing the full signaling complex to assemble.

Example 5

Design of Circularly Permutated IL-2 Fused to IL-2Rα (RDB1405)

Upon binding IL-2Rα, the binding conformation of IL-2 is stabilized to allow for a high affinity complex to be formed with IL-2Rβ and $\gamma_c$. RDB1405 is designed to be a super agonist of IL-2-mediated signaling, particularly in cells lacking IL-2Rα, as it would be able to form the high affinity complex without requiring binding to cell-associated IL-2Rα. The crystal structure of the quaternary signaling complex of IL-2 (2B5I.pdb; FIG. 8A) was utilized to design a circularly permutated variant of IL-2, such that the engineered C terminus can be fused to the N-terminus of IL-2Rα through a short spacer. Briefly, the engineered N and C termini correspond to residues 95 and 94, respectively, in wild-type IL-2. The native IL-2 C-terminus was joined to residue 4 of IL-2 through a 2 amino acid linker. Finally the newly created C-terminus was fused to the N-terminus of IL-2Rα through a 6 amino acid spacer, and the C-terminus of IL-2Rα was fused to human IgG1 Fc, resulting in RDB1405 (FIG. 8B; SEQ ID NO: 12 (protein) and SEQ ID NO: 13 (nucleic acid)).

Example 6

Design of Circularly Permutated Fusion Proteins

An IL-2 or IL-15 fusion protein with improved selectivity for cells expressing IL-2Rβγ (but not IL-2Rα) over cells expressing IL-2Rαβγ relative wild-type IL-2 (wild-type IL-2 has a higher preference for cells expressing IL-2Rαβγ) was designed. By fusing IL-2Rα to IL-2 or IL-15Rα to IL-15, the resulting fusion protein had greater activity on cells lacking the respective alpha chain (IL-2Rα or IL-15Rα) as compared to the native ligand, and preference for cells expressing the respective alpha chain would be reduced. Thus, the ratio of activity, $EC_{50}(IL\text{-}2R\alpha\beta\gamma^{+})/EC_{50}(IL\text{-}2R\alpha^{-}IL\text{-}2R\beta\gamma^{+})$ would increase for CP-IL-2-IL-2Rα fusion proteins would be less for relative to wild type IL-2. Analogous results would be expected for CP-IL-15-IL-15Rα fusion proteins. Circular permutation of the cytokine is required to appropriately orient the termini in an optimal location for fusion as the native termini are oriented distally to the alpha chains in the signaling complex.

Results:

In cells lacking IL-2Rα, but expressing IL-2Rβγ (HH cell line)[i], the engineered constructs are as effective (in fact, two to five-fold better) as Proleukin in promoting STATS phosphorylation (FIG. 11A, left panel). In contrast, in a cell line expressing the heterotrimeric high affinity receptor complex, IL-2Rαβγ, (CTLL-2 cell line)[ii], two of the engineered constructs (RDB1411, RDB1413) are 100- to 300-fold less active than Proleukin as measured by cell proliferation. Overall, the engineered constructs show between 400 and 600-fold greater selectivity for cells lacking IL-2Rα, relative to wild-type IL-2, and thus have the potential to deliver an improved therapeutic profile. Although the increase in the ratio of activity was observed, as expected, it was surprising, that the greater effect on the increase in the ratio was the dramatic loss of activity (100- to 300-fold) in cells containing IL-2Rα, rather than an enhancement in activity (only 2- to 5-fold) for cells lacking IL-2Rα.

In cells lacking IL-2Rα, but expressing IL-2Rβγ (HH cell line)[i], the engineered constructs are potent activators of STATS phosphorylation, but about 10× less potent than wild-type IL-15 (FIG. 12A, left panel). In a cell line expressing the heterotrimeric high affinity receptor complex, IL-2Rαβγ, (CTLL-2 cell line)[ii], the engineered constructs (RDB1408, RDB1416) are 2000- to 6000-fold less active than wild-type IL-15 as measured by cell proliferation. Overall, the engineered constructs show between 200 and 600-fold greater selectivity for cells lacking IL-2Rα, relative to wild-type IL-15. Although the increase in the ratio of activity was observed, as expected, it was surprising, that the greater effect on the increase in the ratio was the dramatic loss of activity (2000- to 6000-fold) in cells containing IL-2Rα and that a 10-fold loss of activity was observed for cells lacking IL-2Rα.

Constructs:

RDB1409: CP-IL-2(C145S)—FLAG; Circularly permuted IL-2. The C145S mutation is analogous to that in Proleukin (rhIL-2) to improve the physical properties of the protein. The FLAG tag is added for ease in purification.

(SEQ ID NO: 24)

```
SKNFHLRPRDLISNINVIVLELKGSETTFMCEYADETATIVEFLNRWIT

FSQSIISTLTGGSSSTKKTQLQLEHLLLDLQMILNGINNYKNPKLTRML

TFKFYMPKKATELKHLQCLEEELKPLEEVLNLAQGSDYKDDDDK
```

RDB1411: CP-IL-2(C145S)-IL-2Rα-Fc; Circularly permuted IL-2 fused to IL-2Rα. The C145S mutation is analogous to that in Proleukin (rhIL-2) to improve the physical properties of the protein. The Fc is added for ease in purification.

(SEQ ID NO: 25)

```
SKNFHLRPRDLISNINVIVLELKGSETTFMCEYADETATIVEFLNRWIT

FSQSIISTLTGGSSSTKKTQLQLEHLLLDLQMILNGINNYKNPKLTRML

TFKFYMPKKATELKHLQCLEEELKPLEEVLNLAQGSGGGSELCDDDPPE

IPHATFKAMAYKEGTMLNCECKRGFRRIKSGSLYMLCTGNSSHSSWDNQ
```

```
-continued
CQCTSSATRNTTKQVTPQPEEQKERKTTEMQSPMQPVDQASLPGHCREP

PPWENEATERIYHFVVGQMVYYQCVQGYRALHRGPAESVCKMTHGKTRW

TQPQLICTGGGGSEPKSSDKTHTCPPCPAPELLGGPSVFLFPPKPKDTL

MISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

RDB1413: CP-IL-2(C145S)-IL-2Rα-FLAG; Circularly permuted IL-2 fused to IL-2Rα. The C145S mutation is analogous to that in Proleukin (rhIL-2) to improve the physical properties of the protein. The FLAG tag is added for ease in purification. Construct analogous to RDB1411, replacing Fc with FLAG.

```
                                          (SEQ ID NO: 26)
SKNFHLRPRDLISNINVIVLELKGSETTFMCEYADETATIVEFLNRWIT

FSQSIISTLTGGSSSTKKTQLQLEHLLLDLQMILNGINNYKNPKLTRML

TFKFYMPKKATELKHLQCLEEELKPLEEVLNLAQGSGGGSELCDDDPPE

IPHATFKAMAYKEGTMLNCECKRGFRRIKSGSLYMLCTGNSSHSSWDNQ

CQCTSSATRNTTKQVTPQPEEQKERKTTEMQSPMQPVDQASLPGHCREP

PPWENEATERIYHFVVGQMVYYQCVQGYRALHRGPAESVCKMTHGKTRW

TQPQLICTGDYKDDDDK
```

RDB1408: Fc-IL-15Rα(sushi)-CP-IL-15; Circularly permuted IL-15 fused to the sushi domain of IL-15Rα. The Fc is added for ease in purification.

```
                                          (SEQ ID NO: 27)
EPKSSDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW
```

```
-continued
LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGKGSITCPPPMSVEH

ADIWVKSYSLYSRERYICNSGFKRKAGTSSLTECVLNKATNVAHWTTPS

LKCIRDGGSELEEKNIKEFLQSFVHIVQMFINGGGSNWVNVISDLKKIE

DLIQSMHIDATLYTESDVHPSCKVTAMKCFLLELQVISLESGDASIHDT

VENLIILANNSLSSNGNVTESGCKEC
```

RDB1416: FLAG-IL-15Rα(sushi)-CP-IL-15; Circularly permuted IL-15 fused to the sushi domain of IL-15Rα. The FLAG tag is added for ease in purification. Construct analogous to RDB1408, replacing Fc with FLAG.

```
                                          (SEQ ID NO: 28)
DYKDDDDKGSITCPPPMSVEHADIWVKSYSLYSRERYICNSGFKRKAGT

SSLTECVLNKATNVAHWTTPSLKCIRDGGSELEEKNIKEFLQSFVHIVQ

MFINGGGSNWVNVISDLKKIEDLIQSMHIDATLYTESDVHPSCKVTAMK

CFLLELQVISLESGDASIHDTVENLIILANNSLSSNGNVTESGCKEC
```

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

```
1)
PRT
RDB1503
1
QNQWLQDMTT  HLILRSFKEF  LQSSLRALRQ  MSGGSGGGSS  ERIDKQIRYI

LDGISALRKE  TCNKSNMCES  SKEALAENNL  NLPKMAEKDG  CFQSGFNEET

CLVKIITGLL  EFEVYLEYLQ  NRFESSEEQA  RAVQMSTKVL  IQFLQKKAKN

LDAITTPDPT  TNASLLTKLQ

2)
DNA
RDB1503
1
CAGAACCAGT  GGCTGCAGGA  CATGACCACC  CACCTGATCC  TGCGGTCCTT

CAAAGAGTTC  CTGCAGTCCT  CCCTGCGGGC  CCTGAGACAG  ATGAGCGGAG

GATCTGGCGG  AGGCTCCTCT  GAGCGGATCG  ACAAGCAGAT  CCGGTACATC

CTGGACGGCA  TCTCCGCCCT  GCGGAAAGAG  ACATGCAACA  AGTCCAACAT

GTGCGAGTCC  AGCAAAGAGG  CCCTGGCCGA  GAACAACCTG  AACCTGCCCA

AGATGGCTGA  GAAGGACGGC  TGCTTCCAGT  CCGGCTTCAA  CGAAGAGACT
```

```
TGCCTGGTCA AGATCATCAC CGGCCTGCTG GAATTTGAGG TGTACCTGGA

ATACCTGCAG AACAGATTCG AGTCCTCCGA GGAACAGGCC AGAGCCGTGC

AGATGTCCAC CAAGGTGCTG ATCCAGTTTC TGCAGAAGAA GGCCAAGAAC

CTGGACGCTA TCACCACCCC CGACCCTACC ACCAATGCCT CCCTGCTGAC

CAAGCTGCAG TGATAA

3)
PRT
IL6
1
MNSFSTSAFG PVAFSLGLLL VLPAAFPAPV PPGEDSKDVA APHRQPLTSS

ERIDKQIRYI LDGISALRKE TCNKSNMCES SKEALAENNL NLPKMAEKDG

CFQSGFNEET CLVKIITGLL EFEVYLEYLQ NRFESSEEQA RAVQMSTKVL

IQFLQKKAKN LDAITTPDPT TNASLLTKLQ AQNQWLQDMT THLILRSFKE

FLQSSLRALR QM

4)
PRT
RDB1527
1
QNQWLQDMTT HLILRSFKEF LQSSLRALRQ MSGGSGGGSS ERIDKQIRYI

LDGISALRKE TCNKSNMCES SKEALAENNL NLPKMAEKDG CFQSGFNEET

CLVKIITGLL EFEVYLEYLQ NRFESSEEQA RAVQMSTKVL IQFLQKKAKN

LDAITTPDPT TNASLLTKLQ ASELLDPCGY ISPESPVVQL HSNFTAVCVL

KEKCMDYFHV NANYIVWKTN HFTIPKEQYT IINRTASSVT FTDIASLNIQ

LTCNILTFGQ LEQNVYGITI ISGLVPRGSE PKSSDKTHTC PPCPAPELLG

GPSVFLFPPK PKDTLMISRT PEVTCVVVDV SHEDPEVKFN WYVDGVEVHN

AKTKPREEQY NSTYRVVSVL TVLHQDWLNG KEYKCKVSNK ALPAPIEKTI

SKAKGQPREP QVYTLPPSRE EMTKNQVSLT CLVKGFYPSD IAVEWESNGQ

PENNYKTTPP VLDSDGSFFL YSKLTVDKSR WQQGNVFSCS VMHEALHNHY

TQKSLSLSPG K

5)
DNA
RDB1527
1
CAAAACCAGT GGCTCCAGGA TATGACCACC CACCTCATCC TCAGAAGTTT

CAAGGAGTTC CTCCAGTCCA GCCTGAGGGC TCTGAGGCAA ATGAGCGGAG

GCTCCGGCGG AGGCAGCTCC GAGAGAATCG ACAAGCAGAT CAGGTACATC

CTCGATGGCA TCAGCGCCCT CAGAAAAGAA ACCTGTAATA AGAGCAACAT

GTGTGAGAGC AGCAAGGAAG CCCTCGCCGA GAACAATCTG AACCTCCCCA

AAATGGCTGA GAAGGACGGA TGCTTCCAGA GCGGCTTCAA TGAGGAGACA

TGCCTCGTGA AGATCATCAC AGGACTCCTG GAGTTCGAAG TCTACCTGGA

GTACCTCCAG AACAGGTTCG AATCCAGCGA GGAACAGGCT AGGGCTGTGC

AGATGTCCAC CAAGGTGCTG ATCCAGTTCC TCCAGAAGAA GGCCAAGAAT

CTGGATGCCA TCACCACACC CGATCCTACA ACCAACGCCA GCCTGCTGAC

CAAGCTCCAG GCCTCCGAAC TCCTGGACCC TTGTGGCTAC ATTTCCCCTG

AAAGCCCTGT GGTGCAACTC CACAGCAATT TCACAGCCGT CTGTGTGCTC

AAGGAGAAGT GCATGGACTA CTTTCACGTG AATGCTAATT ATATCGTGTG
```

-continued

```
GAAGACAAAC CACTTCACCA TCCCCAAGGA GCAGTATACC ATCATCAACA
GGACCGCCTC CAGCGTGACA TTCACCGACA TCGCTTCCCT CAACATTCAG
CTGACCTGCA ATATCCTCAC CTTCGGCCAG CTGGAGCAGA ACGTGTACGG
AATCACCATC ATTAGCGGCC TCGTCCCTAG AGGCTCCGAA CCCAAGTCCT
CCGATAAAAC CCATACCTGC CCCCCTTGCC CTGCTCCCGA ACTCCTCGGC
GGCCCCAGCG TGTTTCTCTT CCCTCCCAAG CCCAAAGATA CCCTGATGAT
CAGCAGGACA CCCGAAGTCA CCTGCGTGGT GGTCGACGTG TCCCACGAGG
ACCCCGAGGT CAAATTCAAC TGGTACGTCG ATGGCGTGGA GGTGCATAAT
GCTAAGACCA AGCCCAGGGA GGAGCAGTAC AACTCCACAT ACAGGGTGGT
CTCCGTCCTG ACCGTGCTGC ATCAAGACTG GCTGAACGGC AAGGAGTATA
AGTGCAAGGT GAGCAATAAA GCCCTCCCCG CCCCTATTGA AAAGACCATT
TCCAAGGCCA AGGGCCAGCC TAGAGAACCT CAAGTCTACA CACTCCCCCC
CTCCAGGGAG GAGATGACCA AAAATCAGGT CTCCCTGACC TGCCTGGTGA
AGGGCTTCTA TCCTAGCGAC ATCGCCGTCG AGTGGGAGAG CAACGGACAG
CCCGAGAACA ACTACAAAAC CACACCTCCC GTGCTCGACA GCGACGGCAG
CTTCTTCCTG TACTCCAAGC TCACCGTGGA TAAGTCCAGG TGGCAGCAAG
GCAACGTGTT TAGCTGCAGC GTGATGCACG AAGCTCTCCA CAACCACTAT
ACCCAGAAGT CCCTCAGCCT CAGCCCTGGC AAGTAGTGA

6)
PRT
RDB1529
1
LTSSERIDKQ IRYILDGISA LRKETCNKSN MCESSKEALA ENNLNLPKMA
EKDGCFQSGF NEETCLVKII TGLLEFEVYL EYLQNRFESS EEQARAVQMS
TKVLIQFLQK KAKNLDAITT PDPTTNASLL TKLQAQNQWL QDMTTHLILR
SFKEFLQSSL RALRQMSELL DPCGYISPES PVVQLHSNFT AVCVLKEKCM
DYFHVNANYI VWKTNHFTIP KEQYTIINRT ASSVTFTDIA SLNIQLTCNI
LTFGQLEQNV YGITIISGLV PRGSEPKSSD KTHTCPPCPA PELLGGPSVF
LFPPKPKDTL MISRTPEVTC VVVDVSHEDP EVKFNWYVDG VEVHNAKTKP
REEQYNSTYR VVSVLTVLHQ DWLNGKEYKC KVSNKALPAP IEKTISKAKG
QPREPQVYTL PPSREEMTKN QVSLTCLVKG FYPSDIAVEW ESNGQPENNY
KTTPPVLDSD GSFFLYSKLT VDKSRWQQGN VFSCSVMHEA LHNHYTQKSL SLSPGK

7)
DNA
RDB1529
1
CTGACCTCCA GCGAAAGGAT CGACAAGCAG ATCAGGTACA TCCTCGACGG
CATCTCCGCT CTCAGAAAGG AGACCTGCAA CAAGAGCAAC ATGTGCGAGA
GCAGCAAGGA AGCCCTGGCT GAGAACAATC TCAACCTGCC AAGATGGCC
GAAAAGGATG GATGCTTCCA GAGCGGCTTT AACGAGGAGA CCTGCCTCGT
GAAGATCATC ACCGGCCTGC TCGAGTTTGA GGTGTATCTC GAGTACCTGC
AGAATAGGTT CGAGAGCAGC GAGGAACAGG CTAGAGCTGT CCAGATGTCC
ACCAAGGTGC TGATCCAGTT CCTGCAAAAG AAGGCCAAGA ATCTCGACGC
TATCACCACC CCTGACCCTA CCACAAACGC CAGCCTGCTG ACCAAGCTGC
AGGCCCAAAA CCAATGGCTC CAGGACATGA CAACCCACCT GATCCTGAGG
```

```
AGCTTCAAGG AGTTCCTCCA ATCCTCCCTC AGGGCCCTGA GACAGATGAG

CGAACTGCTC GACCCTTGTG GATACATTAG CCCTGAATCC CCCGTGGTGC

AGCTGCATAG CAATTTCACC GCCGTGTGCG TGCTCAAAGA GAAGTGCATG

GACTACTTCC ATGTGAACGC CAACTACATC GTGTGGAAGA CCAACCATTT

CACCATCCCC AAGGAGCAAT ACACCATCAT CAACAGAACC GCCAGCAGCG

TCACATTCAC CGACATCGCC TCCCTGAACA TCCAACTGAC ATGCAACATT

CTCACCTTCG GCCAGCTGGA GCAAAATGTG TACGGCATCA CCATCATTAG

CGGCCTCGTC CCTAGAGGCT CCGAACCCAA GTCCTCCGAT AAAACCCATA

CCTGCCCCCC TTGCCCTGCT CCCGAACTCC TCGGCGGCCC CAGCGTGTTT

CTCTTCCCTC CCAAGCCCAA AGATACCCTG ATGATCAGCA GGACACCCGA

AGTCACCTGC GTGGTGGTCG ACGTGTCCCA CGAGGACCCC GAGGTCAAAT

TCAACTGGTA CGTCGATGGC GTGGAGGTGC ATAATGCTAA GACCAAGCCC

AGGGAGGAGC AGTACAACTC CACATACAGG GTGGTCTCCG TCCTGACCGT

GCTGCATCAA GACTGGCTGA ACGGCAAGGA GTATAAGTGC AAGGTGAGCA

ATAAAGCCCT CCCCGCCCCT ATTGAGAAGA CCATTTCCAA GGCCAAGGGC

CAGCCTAGAG AACCTCAAGT CTACACACTC CCCCCCTCCA GGGAGGAGAT

GACCAAAAAT CAGGTCTCCC TGACCTGCCT GGTGAAGGGC TTCTATCCTA

GCGACATCGC CGTCGAGTGG GAGAGCAACG GACAGCCCGA GAACAACTAC

AAAACCACAC CTCCCGTGCT CGACAGCGAC GGCAGCTTCT TCCTGTACTC

CAAGCTCACC GTGGATAAGT CCAGGTGGCA GCAAGGCAAC GTGTTTAGCT

GCAGCGTGAT GCACGAAGCT CTCCACAACC ACTATACCCA GAAGTCCCTC

AGCCTCAGCC CTGGCAAGTA GTGA

8)
PRT
RDB1515
1
EKNLYLSCVL KDDKPTLQLE SVDPKNYPKK KMEKRFVFNK IEINNKLEFE

SAQFPNWYIS TSQAENMPVF LGGTKGGQDI TDFTMQFVSS GGSGGSGAPV

RSLNCTLRDS QQKSLVMSGP YELKALHLQG QDMEQQVVFS MSFVQGEESN

DKIPVALGLK

9)
DNA
RDB1515
1
GAGAAGAACC TCTACCTCTC CTGCGTGCTG AAGGACGACA AGCCCACACT

CCAGCTGGAG TCCGTGGACC CCAAGAACTA CCCCAAGAAG AAGATGGAGA

AGCGGTTCGT GTTCAACAAG ATCGAGATCA ACAACAAGCT GGAGTTCGAG

AGCGCCCAGT TCCCCAACTG GTACATTTCC ACCTCCCAGG CCGAGAACAT

GCCCGTCTTT CTGGGCGGAA CCAAGGGCGG CCAGGACATC ACCGACTTCA

CCATGCAGTT CGTCTCCAGC GGAGGAAGCG GAGGCAGCGG AGCTCCCGTG

AGGAGCCTGA ACTGCACCCT GAGGGACAGC CAGCAGAAGT CCCTGGTGAT

GTCCGGACCC TACGAACTGA AGGCCCTCCA TCTGCAAGGA CAGGATATGG

AGCAGCAGGT GGTGTTCTCC ATGTCCTTCG TCCAGGGCGA AGAGTCCAAC

GACAAGATCC CCGTGGCCCT GGGCCTGAAA TAGTGA
```

10)
PRT
RDB1538
1
MDAMKRGLCC VLLLCGAVFV SARDYKDDDD KDKCKEREEK IILVSSANEI

DVRPCPLNPN EHKGTITWYK DDSKTPVSTE QASRIHQHKE KLWFVPAKVE

DSGHYYCVVR NSSYCLRIKI SAKFVENEPN LCYNAQAIFK QKLPVAGDGG

LVCPYMEFFK NENNELPKLQ WYKDCKPLLL DNIHFSGVKD RLIVMNVAEK

HRGNYTCHAS YTYLGKQYPI TRVIEFITLE ENSGGSGNKL EFESAQFPNW

YISTSQAENM PVFLGGTKGG QDITDFTMQF VSSGGSGGSG APVRSLNCTL

RDSQQKSLVM SGPYELKALH LQGQDMEQQV VFSMSFVQGE ESNDKIPVAL

GLKEKNLYLS CVLKDDKPTL QLESVDPKNY PKKKMEKRFV FNKIEIN

11)
DNA
RDB1538
1
ATGGACGCTA TGAAGCGGGG ACTGTGCTGC GTGCTCCTGC TGTGCGGCGC

TGTCTTTGTC AGCGCCCGGG ACTATAAGGA CGATGATGAC AAGGACAAGT

GCAAGGAGCG GGAGGAGAAG ATCATCCTGG TGAGCTCCGC AACGAGATT

GACGTCCGGC CCTGCCCTCT CAACCCCAAC GAGCATAAGG CACCATCAC

CTGGTACAAA GACGACAGCA AAACACCCGT CTCCACCGAG CAAGCCTCCC

GGATTCACCA GCACAAGGAG AAGCTCTGGT TCGTGCCCGC TAAGGTGGAG

GATTCCGGAC ACTACTACTG TGTGGTCCGG AACTCCAGCT ACTGCCTGAG

GATTAAGATC AGCGCTAAGT TCGTCGAGAA CGAGCCCAAC CTCTGCTACA

ATGCCCAGGC CATCTTCAAG CAGAAGCTCC CTGTGGCTGG AGACGGAGGC

CTGGTCTGCC CCTACATGGA GTTCTTCAAG AACGAGAATA ACGAGCTGCC

TAAGCTGCAG TGGTACAAGG ACTGCAAACC CCTGCTCCTC GACAACATCC

ACTTCTCCGG CGTCAAGGAC CGGCTGATCG TCATGAACGT GGCCGAGAAG

CACAGGGGCA ACTATACCTG TCACGCCAGC TACACCTACC TGGGAAAGCA

GTATCCTATC ACCAGGGTGA TTGAGTTCAT CACACTCGAG GAAAACAGCG

GCGGCAGCGG CAACAAGCTG GAGTTCGAGT CCGCCCAGTT TCCTAACTGG

TACATCTCCA CAAGCCAGGC CGAGAACATG CCTGTCTTCC TGGGCGGCAC

CAAAGGCGGC CAAGATATCA CCGACTTCAC CATGCAGTTT GTGAGCTCCG

GAGGCTCCGG AGGAAGCGGA GCTCCTGTGC GGTCCCTGAA TTGCACCCTG

CGGGATTCCC AACAGAAGAG CCTGGTGATG TCCGGCCCCT ACGAGCTCAA

GGCCCTCCAT CTGCAAGGCC AGGACATGGA GCAGCAGGTG GTCTTCAGCA

TGAGCTTCGT GCAGGGAGAG GAGTCCAACG ATAAGATCCC CGTCGCTCTC

GGACTCAAGG AGAAGAACCT GTACCTCTCC TGCGTGCTGA AGGACGATAA

GCCCACCCTC CAGCTGGAAT CCGTGGACCC CAAGAACTAC CCCAAGAAAA

AAATGGAAAA GCGGTTTGTC TTTAACAAGA TCGAGATTAA CTAGTGA

12)
PRT
RDB1405
1
SKNFHLRPRD LISNINVIVL ELKGSETTFM CEYADETATI VEFLNRWITF

CQSIISTLTG GSSSTKKTQL QLEHLLLDLQ MILNGINNYK NPKLTRMLTF

KFYMPKKATE LKHLQCLEEE LKPLEEVLNL AQSGGGSEL CDDDPPEIPH

```
ATFKAMAYKE GTMLNCECKR GFRRIKSGSL YMLCTGNSSH SSWDNQCQCT

SSATRNTTKQ VTPQPEEQKE RKTTEMQSPM QPVDQASLPG HCREPPPWEN

EATERIYHFV VGQMVYYQCV QGYRALHRGP AESVCKMTHG KTRWTQPQLI

CTGGGGSEPK SSDKTHTCPP CPAPELLGGP SVFLFPPKPK DTLMISRTPE

VTCVVVDVSH EDPEVKFNWY VDGVEVHNAK TKPREEQYNS TYRVVSVLTV

LHQDWLNGKE YKCKVSNKAL PAPIEKTISK AKGQPREPQV YTLPPSREEM

TKNQVSLTCL VKGFYPSDIA VEWESNGQPE NNYKTTPPVL DSDGSFFLYS

KLTVDKSRWQ QGNVFSCSVM HEALHNHYTQ KSLSLSPGK

13)
DNA
RDB1405
1
TCCAAGAACT TCCACCTGAG GCCTCGGGAC CTGATCTCCA ACATCAACGT

GATCGTGCTG GAACTGAAGG CTCCGAGAC AACCTTCATG TGCGAGTACG

CCGACGAGAC AGCTACCATC GTGGAATTTC TGAACCGGTG GATCACCTTC

TGCCAGTCCA TCATCTCCAC CCTGACCGGC GGCTCCTCCA GCACCAAGAA

AACCCAGCTG CAGCTGGAAC ATCTGCTGCT GGACCTGCAG ATGATCCTGA

ACGGCATCAA CAACTACAAG AACCCCAAGC TGACCCGGAT GCTGACCTTC

AAGTTCTACA TGCCCAAGAA GGCCACCGAA CTGAAACATC TGCAGTGCCT

GGAAGAAGAA CTGAAGCCCC TGGAAGAGGT GCTGAACCTG GCTCAGGGAT

CTGGCGGCGG ATCTGAGCTG TGCGACGACG ACCCTCCTGA GATCCCTCAC

GCCACCTTCA AGGCCATGGC TTACAAAGAG GGCACCATGC TGAACTGCGA

GTGCAAGAGA GGCTTCCGGC GGATCAAGTC CGGCTCCCTG TACATGCTGT

GCACCGGCAA CTCCAGCCAC TCCTCCTGGG ACAACCAGTG CCAGTGCACC

TCCTCTGCCA CCCGGAACAC CACCAAACAA GTGACCCCCC AGCCCGAGGA

ACAGAAAGAG CGCAAGACCA CCGAGATGCA GTCCCCCATG CAGCCTGTGG

ACCAGGCTTC TCTGCCTGGC CACTGCAGAG AGCCTCCACC TTGGGAGAAC

GAGGCTACCG AGAGAATCTA CCACTTCGTC GTGGGCCAGA TGGTGTACTA

CCAGTGCGTG CAGGGCTACC GCGCCCTGCA TAGAGGACCT GCTGAGTCCG

TGTGCAAGAT GACCCACGGC AAGACCCGGT GGACCCAGCC TCAGCTGATC

TGTACAGGCG GCGGAGGCTC CGAGCCTAAG TCCTCCGATA AGACCCACAC

CTGTCCCCCC TGTCCTGCCC CTGAACTGCT GGGAGGCCCT TCCGTGTTCC

TGTTCCCCCC AAAGCCCAAG GACACCCTGA TGATCTCCCG GACCCCCGAA

GTGACCTGCG TGGTGGTGGA TGTGTCCCAC GAGGACCCTG AAGTGAAGTT

CAATTGGTAC GTGGACGGCG TGGAAGTGCA CAACGCCAAG ACCAAGCCCA

GAGAGGAACA GTACAACTCC ACCTACCGGG TGGTGTCCGT GCTGACCGTG

CTGCACCAGG ATTGGCTGAA TGGCAAAGAG TACAAGTGCA AGGTGTCCAA

CAAGGCCCTG CCAGCCCCCA TCGAAAAGAC CATCTCCAAG GCCAAGGGCC

AGCCCCGGGA ACCCCAGGTG TACACACTGC CCCCTAGCCG GGAAGAGATG

ACCAAGAACC AGGTGTCCCT GACCTGTCTC GTGAAGGGCT TCTACCCCTC

CGATATCGCC GTGGAATGGG AGTCCAACGG CCAGCCTGAG AACAATTATA

AGACCACCCC CCCTGTGCTG GACTCCGACG GCTCATTCTT CCTGTACAGC
```

-continued

AAGCTGACAG TGGACAAGTC CCGGTGGCAG CAGGGCAACG TGTTCTCCTG

CTCCGTGATG CACGAGGCCC TGCACAACCA CTACACCCAG AAGTCCCTGT

CCCTGTCTCC CGGCAAGTGA TGA

14)
PRT
Linker
1
SGGSGGG

15)
PRT
Linker
1
GGSGGSG

16)
PRT
Linker
1
GG

17)
PRT
Stability sequence
1
MG

18)
PRT
Stability sequence
1
MGG

19)
PRT
IL-1β
1
MAEVPELASE MMAYYSGNED DLFFEADGPK QMKCSFQDLD LCPLDGGIQL

RISDHHYSKG FRQAASVVVA MDKLRKMLVP CPQTFQENDL STFFPFIFEE

EPIFFDTWDN EAYVHDAPVR SLNCTLRDSQ QKSLVMSGPY ELKALHLQGQ

DMEQQVVFSM SFVQGEESND KIPVALGLKE KNLYLSCVLK DDKPTLQLES

VDPKNYPKKK MEKRFVFNKI EINNKLEFES AQFPNWYIST SQAENMPVFL

GGTKGGQDIT DFTMQFVSS

20)
PRT
IL-2
1
MYRMQLLSCI ALSLALVTNS APTSSSTKKT QLQLEHLLLD LQMILNGINN

YKNPKLTRML TFKFYMPKKA TELKHLQCLE EELKPLEEVL NLAQSKNFHL

RPRDLISNIN VIVLELKGSE TTFMCEYADE TATIVEFLNR WITFCQSIIS

TLT

21)
PRT
gp130
1
MLTLQTWVVQ ALFIFLTTES TGELLDPCGY ISPESPVVQL HSNFTAVCVL

KEKCMDYFHV NANYIVWKTN HFTIPKEQYT IINRTASSVT FTDIASLNIQ

LTCNILTFGQ LEQNVYGITI ISGLPPEKPK NLSCIVNEGK KMRCEWDGGR

ETHLETNFTL KSEWATHKFA DCKAKRDTPT SCTVDYSTVY FVNIEVWVEA

ENALGKVTSD HINFDPVYKV KPNPPHNLSV INSEELSSIL KLTWTNPSIK

SVIILKYNIQ YRTKDASTWS QIPPEDTAST RSSFTVQDLK PFTEYVFRIR

CMKEDGKGYW SDWSEEASGI TYEDRPSKAP SFWYKIDPSH TQGYRTVQLV

```
WKTLPPFEAN GKILDYEVTL TRWKSHLQNY TVNATKLTVN LTNDRYLATL

TVRNLVGKSD AAVLTIPACD FQATHPVMDL KAFPKDNMLW VEWTTPRESV

KKYILEWCVL SDKAPCITDW QQEDGTVHRT YLRGNLAESK CYLITVTPVY

ADGPGSPESI KAYLKQAPPS KGPTVRTKKV GKNEAVLEWD QLPVDVQNGF

IRNYTIFYRT IIGNETAVNV DSSHTEYTLS SLTSDTLYMV RMAAYTDEGG

KDGPEFTFTT PKFAQGEIEA IVVPVCLAFL LTTLLGVLFC FNKRDLIKKH

IWPNVPDPSK SHIAQWSPHT PPRHNFNSKD QMYSDGNFTD VSVVEIEAND

KKPFPEDLKS LDLFKKEKIN TEGHSSGIGG SSCMSSSRPS ISSSDENESS

QNTSSTVQYS TVVHSGYRHQ VPSVQVFSRS ESTQPLLDSE ERPEDLQLVD

HVDGGDGILP RQQYFKQNCS QHESSPDISH FERSKQVSSV NEEDFVRLKQ

QISDHISQSC GSGQMKMFQE VSAADAFGPG TEGQVERFET VGMEAATDEG

MPKSYLPQTV RQGGYMPQ

22)
PRT
IL-1RI
1
MKVLLRLICF IALLISSLEA DKCKEREEKI ILVSSANEID VRPCPLNPNE

HKGTITWYKD DSKTPVSTEQ ASRIHQHKEK LWFVPAKVED SGHYYCVVRN

SSYCLRIKIS AKFVENEPNL CYNAQAIFKQ NLPVAGDGGL VCPYMEFFKN

ENNELPKLQW YKDCKPLLLD NIHFSGVKDR LIVMNVAEKH RGNYTCHASY

TYLGKQYPIT RVIEFITLEE NKPTRPVIVS PANETMEVDL GSQIQLICNV

TGQLSDIAYW KWNGSVIDED DPVLGEDYYS VENPANKRRS TLITVLNISE

IESRFYKHPF TCFAKNTHGI DAAYIQLIYP VTNFQKHMIG ICVTLTVIIV

CSVFIYKIFK IDIVLWYRDS CYDFLPIKAS DGKTYDAYIL YPKTVGEGST

SDCDIFVFKV LPEVLEKQCG YKLFIYGRDD YVGEDIVEVI NENVKKSRRL

IIILVRETSS FSWLGGSSEE QIAMYNALVQ DGIKVVLLEL EKIQDYEKMP

ESIKFIKQKH GAIRWSGDFT QGPQSAKTRF WKNVRYHMPV QRRSPSSKHQ

LLSPATKEKL QREAHVPLG

23)
PRT
IL-2Rα
1
MDSYLLMWGL LTFIMVPGCQ AELCDDDPPE IPHATFKAMA YKEGTMLNCE

CKRGFRRIKS GSLYMLCTGN SSHSSWDNQC QCTSSATRNT TKQVTPQPEE

QKERKTTEMQ SPMQPVDQAS LPGHCREPPP WENEATERIY HFVVGQMVYY

QCVQGYRALH RGPAESVCKM THGKTRWTQP QLICTGEMET SQFPGEEKPQ

ASPEGRPESE TSCLVTTTDF QIQTEMAATM ETSIFTTEYQ VAVAGCVFLL

ISVLLLSGLT WQRRQRKSRR TI
```

---

What is claimed is:

1. A fusion polypeptide comprising, a first polypeptide fusion partner linked to a modified ligand corresponding to all or a portion of a native ligand of a target receptor, wherein the modified ligand has been circularly permuted to create a new N-terminus and a new C-terminus as compared to the native ligand, and wherein the new N-terminus or the new C-terminus of the modified ligand is linked to a first polypeptide fusion partner to form a fusion polypeptide wherein the new C-terminus and the new N-terminus of the modified ligand do not disrupt any binding domain of the modified ligand for the target receptor and wherein the modified ligand optionally has increased affinity for the target receptor as compared to the native ligand for the receptor, wherein the target receptor functions by stepwise formation of a multimeric activation complex to trigger signal transduction of a signaling cellular pathway and wherein when the fusion polypeptide binds the receptor it either enhances the stepwise formation of the multimeric activation complex thereby super agonizing signal transduction by the target receptor or it sterically hinders the stepwise formation of the multimeric complex thereby antagonizing signal transduction by the target receptor wherein the fusion polypeptide comprises amino acids 1-303 of SEQ ID NO: 26.

2. A fusion polypeptide consisting of amino acids 1-303 of SEQ ID NO: 26.

3. A fusion polypeptide comprising amino acids 1-303 of SEQ ID NO: 26.

* * * * *

SEQUENCE LISTING

<160> NUMBER OF SEQ ID NOS: 28

<210> SEQ ID NO 1
<211> LENGTH: 170
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 1

Gln Asn Gln Trp Leu Gln Asp Met Thr Thr His Leu Ile Leu Arg Ser
1               5                   10                  15

Phe Lys Glu Phe Leu Gln Ser Ser Leu Arg Ala Leu Arg Gln Met Ser
            20                  25                  30

Gly Gly Ser Gly Gly Ser Ser Glu Arg Ile Asp Lys Gln Ile Arg
        35                  40                  45

Tyr Ile Leu Asp Gly Ile Ser Ala Leu Arg Lys Glu Thr Cys Asn Lys
    50                  55                  60

Ser Asn Met Cys Glu Ser Ser Lys Glu Ala Leu Ala Glu Asn Asn Leu
65              70                  75                  80

Asn Leu Pro Lys Met Ala Glu Lys Asp Gly Cys Phe Gln Ser Gly Phe
                85                  90                  95

Asn Glu Glu Thr Cys Leu Val Lys Ile Ile Thr Gly Leu Leu Glu Phe
            100                 105                 110

Glu Val Tyr Leu Glu Tyr Leu Gln Asn Arg Phe Glu Ser Ser Glu Glu
        115                 120                 125

Gln Ala Arg Ala Val Gln Met Ser Thr Lys Val Leu Ile Gln Phe Leu
    130                 135                 140

Gln Lys Lys Ala Lys Asn Leu Asp Ala Ile Thr Thr Pro Asp Pro Thr
145                 150                 155                 160

Thr Asn Ala Ser Leu Leu Thr Lys Leu Gln
                165                 170

<210> SEQ ID NO 2
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cagaaccagt ggctgcagga catgaccacc cacctgatcc tgcggtcctt caaagagttc      60
ctgcagtcct ccctgcgggc cctgagacag atgagcggag gatctggcgg aggtcctct     120 gagcggatcg acaagcagat ccggtacatc ctggacggca tctccgccct gcggaaagag     180
acatgcaaca gtccaacat gtgcgagtcc agcaaagagg ccctggccga aaacaacctg     240
aacctgccca agatggctga aaggacggc tgcttccagt ccggcttcaa cgaagagact     300
tgcctggtca agatcatcac cggcctgctg gaatttgagg tgtacctgga atacctgcag     360
aacagattcg agtcctccga ggaacaggcc agagccgtgc agatgtccac caaggtgctg     420
atccagtttc tgcagaagaa ggccaagaac ctggacgcta tcaccacccc cgaccctacc     480
accaatgcct ccctgctgac caagctgcag tgataa                              516

<210> SEQ ID NO 3
<211> LENGTH: 212
<212> TYPE: PRT
<213> ORGANISM: Homo sapiens

<400> SEQUENCE: 3

Met Asn Ser Phe Ser Thr Ser Ala Phe Gly Pro Val Ala Phe Ser Leu
1               5                   10                  15
```

```
Gly Leu Leu Leu Val Leu Pro Ala Ala Phe Pro Ala Pro Val Pro Pro
             20                  25                  30

Gly Glu Asp Ser Lys Asp Val Ala Ala Pro His Arg Gln Pro Leu Thr
         35                  40                  45

Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 4
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Asn Gln Trp Leu Gln Asp Met Thr Thr His Leu Ile Leu Arg Ser
 1               5                  10                  15

Phe Lys Glu Phe Leu Gln Ser Ser Leu Arg Ala Leu Arg Gln Met Ser
             20                  25                  30

Gly Gly Ser Gly Gly Gly Ser Ser Glu Arg Ile Asp Lys Gln Ile Arg
         35                  40                  45

Tyr Ile Leu Asp Gly Ile Ser Ala Leu Arg Lys Glu Thr Cys Asn Lys
 50                  55                  60

Ser Asn Met Cys Glu Ser Ser Lys Glu Ala Leu Ala Glu Asn Asn Leu
 65                  70                  75                  80

Asn Leu Pro Lys Met Ala Glu Lys Asp Gly Cys Phe Gln Ser Gly Phe
                 85                  90                  95

Asn Glu Glu Thr Cys Leu Val Lys Ile Ile Thr Gly Leu Leu Glu Phe
            100                 105                 110

Glu Val Tyr Leu Glu Tyr Leu Gln Asn Arg Phe Glu Ser Ser Glu Glu
        115                 120                 125

Gln Ala Arg Ala Val Gln Met Ser Thr Lys Val Leu Ile Gln Phe Leu
130                 135                 140

Gln Lys Lys Ala Lys Asn Leu Asp Ala Ile Thr Thr Pro Asp Pro Thr
145                 150                 155                 160
```

```
Thr Asn Ala Ser Leu Leu Thr Lys Leu Gln Ala Ser Glu Leu Leu Asp
            165                 170                 175

Pro Cys Gly Tyr Ile Ser Pro Glu Ser Pro Val Val Gln Leu His Ser
        180                 185                 190

Asn Phe Thr Ala Val Cys Val Leu Lys Glu Lys Cys Met Asp Tyr Phe
    195                 200                 205

His Val Asn Ala Asn Tyr Ile Val Trp Lys Thr Asn His Phe Thr Ile
210                 215                 220

Pro Lys Glu Gln Tyr Thr Ile Ile Asn Arg Thr Ala Ser Ser Val Thr
225                 230                 235                 240

Phe Thr Asp Ile Ala Ser Leu Asn Ile Gln Leu Thr Cys Asn Ile Leu
                245                 250                 255

Thr Phe Gly Gln Leu Glu Gln Asn Val Tyr Gly Ile Thr Ile Ile Ser
            260                 265                 270

Gly Leu Val Pro Arg Gly Ser Glu Pro Lys Ser Ser Asp Lys Thr His
        275                 280                 285

Thr Cys Pro Pro Cys Pro Ala Pro Glu Leu Leu Gly Gly Pro Ser Val
    290                 295                 300

Phe Leu Phe Pro Pro Lys Pro Lys Asp Thr Leu Met Ile Ser Arg Thr
305                 310                 315                 320

Pro Glu Val Thr Cys Val Val Val Asp Val Ser His Glu Asp Pro Glu
                325                 330                 335

Val Lys Phe Asn Trp Tyr Val Asp Gly Val Glu Val His Asn Ala Lys
            340                 345                 350

Thr Lys Pro Arg Glu Glu Gln Tyr Asn Ser Thr Tyr Arg Val Val Ser
        355                 360                 365

Val Leu Thr Val Leu His Gln Asp Trp Leu Asn Gly Lys Glu Tyr Lys
    370                 375                 380

Cys Lys Val Ser Asn Lys Ala Leu Pro Ala Pro Ile Glu Lys Thr Ile
385                 390                 395                 400

Ser Lys Ala Lys Gly Gln Pro Arg Glu Pro Gln Val Tyr Thr Leu Pro
                405                 410                 415

Pro Ser Arg Glu Glu Met Thr Lys Asn Gln Val Ser Leu Thr Cys Leu
            420                 425                 430

Val Lys Gly Phe Tyr Pro Ser Asp Ile Ala Val Glu Trp Glu Ser Asn
        435                 440                 445

Gly Gln Pro Glu Asn Asn Tyr Lys Thr Thr Pro Pro Val Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys
            500                 505                 510

<210> SEQ ID NO 5
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
caaaaccagt ggctccagga tatgaccacc cacctcatcc tcagaagttt caaggagttc        60
```

```
ctccagtcca gcctgagggc tctgaggcaa atgagcggag gctccggcgg aggcagctcc      120
gagagaatcg acaagcagat caggtacatc ctcgatggca tcagcgccct cagaaaagaa      180
acctgtaata gagcaacatg tgtgagagc agcaaggaag ccctcgccga gaacaatctg       240
aacctcccca aatggctga aaggacgga tgcttccaga gcggcttcaa tgaggagaca        300
tgcctcgtga agatcatcac aggactcctg gagttcgaag tctacctgga gtacctccag      360
aacaggttcg aatccagcga ggaacaggct agggctgtgc agatgtccac caaggtgctg      420
atccagttcc tccagaagaa ggccaagaat ctggatgcca tcaccacacc cgatcctaca      480
accaacgcca gctgctgac caagctccag gcctccgaac tcctggaccc ttgtggctac       540
atttcccctg aaagccctgt ggtgcaactc acagcaatt tcacagccgt ctgtgtgctc       600
aaggagaagt gcatggacta ctttcacgtg aatgctaatt atatcgtgtg aagacaaac      660
cacttcacca tccccaagga gcagtatacc atcatcaaca ggaccgcctc cagcgtgaca      720
ttcaccgaca tcgcttccct caacattcag ctgacctgca atatcctcac cttcggccag      780
ctggagcaga acgtgtacgg aatcaccatc attagcggcc tcgtccctag aggctccgaa      840
cccaagtcct ccgataaaac ccataccctgc cccccttgcc ctgctcccga actcctcggc      900
ggccccagcg tgtttctctt ccctcccaag cccaaagata ccctgatgat cagcaggaca      960
cccgaagtca cctgcgtggt ggtcgacgtg tcccacgagg accccgaggt caaattcaac     1020
tggtacgtcg atggcgtgga ggtgcataat gctaagacca gcccaggga ggagcagtac      1080
aactccacat acagggtggt ctccgtcctg accgtgctgc atcaagactg gctgaacggc      1140
aaggagtata agtgcaaggt gagcaataaa gccctccccg cccctattga aagaccatt      1200
tccaaggcca agggcagcc tagagaacct caagtctaca cactcccccc ctccagggag      1260
gagatgacca aaaatcaggt ctccctgacc tgcctggtga agggcttcta tcctagcgac     1320
atcgccgtcg agtgggagag caacggacag cccgagaaca actacaaaac cacacctccc     1380
gtgctcgaca gcgacggcag cttcttcctg tactccaagc tcaccgtgga taagtccagg     1440
tggcagcaag cgaacgtgtt tagctgcagc gtgatgcacg aagctctcca caaccactat     1500
acccagaagt ccctcagcct cagccctggc aagtagtga                            1539
```

<210> SEQ ID NO 6
<211> LENGTH: 506
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 6

```
Leu Thr Ser Ser Glu Arg Ile Asp Lys Gln Ile Arg Tyr Ile Leu Asp
1               5                   10                  15

Gly Ile Ser Ala Leu Arg Lys Glu Thr Cys Asn Lys Ser Asn Met Cys
            20                  25                  30

Glu Ser Ser Lys Glu Ala Leu Ala Glu Asn Asn Leu Asn Leu Pro Lys
        35                  40                  45

Met Ala Glu Lys Asp Gly Cys Phe Gln Ser Gly Phe Asn Glu Glu Thr
    50                  55                  60

Cys Leu Val Lys Ile Ile Thr Gly Leu Leu Glu Phe Glu Val Tyr Leu
65                  70                  75                  80

Glu Tyr Leu Gln Asn Arg Phe Glu Ser Ser Glu Glu Gln Ala Arg Ala
                85                  90                  95
```

```
Val Gln Met Ser Thr Lys Val Leu Ile Gln Phe Leu Gln Lys Lys Ala
            100                 105                 110

Lys Asn Leu Asp Ala Ile Thr Thr Pro Asp Pro Thr Thr Asn Ala Ser
            115                 120                 125

Leu Leu Thr Lys Leu Gln Ala Gln Asn Gln Trp Leu Gln Asp Met Thr
130                 135                 140

Thr His Leu Ile Leu Arg Ser Phe Lys Glu Phe Leu Gln Ser Ser Leu
145                 150                 155                 160

Arg Ala Leu Arg Gln Met Ser Glu Leu Leu Asp Pro Cys Gly Tyr Ile
                165                 170                 175

Ser Pro Glu Ser Pro Val Val Gln Leu His Ser Asn Phe Thr Ala Val
            180                 185                 190

Cys Val Leu Lys Glu Lys Cys Met Asp Tyr Phe His Val Asn Ala Asn
            195                 200                 205

Tyr Ile Val Trp Lys Thr Asn His Phe Thr Ile Pro Lys Glu Gln Tyr
210                 215                 220

Thr Ile Ile Asn Arg Thr Ala Ser Ser Val Thr Phe Thr Asp Ile Ala
225                 230                 235                 240

Ser Leu Asn Ile Gln Leu Thr Cys Asn Ile Leu Thr Phe Gly Gln Leu
                245                 250                 255

Glu Gln Asn Val Tyr Gly Ile Thr Ile Ile Ser Gly Leu Val Pro Arg
            260                 265                 270

Gly Ser Glu Pro Lys Ser Ser Asp Lys Thr His Thr Cys Pro Pro Cys
            275                 280                 285

Pro Ala Pro Glu Leu Leu Gly Gly Pro Ser Val Phe Leu Phe Pro Pro
290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
            435                 440                 445

Asn Tyr Lys Thr Thr Pro Pro Val Leu Asp Ser Asp Gly Ser Phe Phe
            450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505
```

<210> SEQ ID NO 7
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
ctgacctcca gcgaaaggat cgacaagcag atcaggtaca tcctcgacgg catctccgct      60
ctcagaaagg agacctgcaa caagagcaac atgtgcgaga gcagcaagga agccctggct     120
gagaacaatc tcaacctgcc caagatggcc gaaaaggatg gatgcttcca gagcggcttt     180
aacgaggaga cctgcctcgt gaagatcatc accggcctgc tcgagtttga ggtgtatctc     240
gagtacctgc agaataggtt cgagagcagc gaggaacagg ctagagctgt ccagatgtcc     300
accaaggtgc tgatccagtt cctgcaaaag aaggccaaga atctcgacgc tatcaccacc     360
cctgacccta ccacaaacgc cagcctgctg accaagctgc aggcccaaaa ccaatggctc     420
caggacatga aacccacct gatcctgagg agcttcaagg agttcctcca atcctccctc     480
agggccctga cagatgag cgaactgctc gacccttgtg atacattag ccctgaatcc     540
cccgtggtgc agctgcatag caatttcacc gccgtgtgcg tgctcaaaga aagtgcatg     600
gactacttcc atgtgaacgc caactacatc gtgtggaaga ccaaccattt caccatcccc     660
aaggagcaat acaccatcat caacagaacc gccagcagcg tcacattcac cgacatcgcc     720
tccctgaaca tccaactgac atgcaacatt ctcaccttcg ccagctgga gcaaaatgtg     780
tacggcatca ccatcattag cggcctcgtc cctagaggct ccgaacccaa gtcctccgat     840
aaaacccata cctgccccc ttgccctgct ccgaactcc tcggcggccc cagcgtgttt     900
ctcttcctc ccaagcccaa agataccctg atgatcagca ggacacccga gtcacctgc      960
gtggtggtcg acgtgtccca cgaggacccc gaggtcaaat tcaactggta cgtcgatggc    1020
gtggaggtgc ataatgctaa gaccaagccc agggaggagc agtacaactc cacatacagg    1080
gtggtctccg tcctgaccgt gctgcatcaa gactggctga acggcaagga gtataagtgc    1140
aaggtgagca ataaagccct ccccgcccct attgagaaga cccatttccaa ggccaagggc    1200
cagcctagag aacctcaagt ctacacactc ccccctcca gggaggagat gaccaaaaat    1260
caggtctccc tgacctgcct ggtgaagggc ttctatccta gcgacatcgc cgtcgagtgg    1320
gagagcaacg gacagcccga gaacaactac aaaaccacac ctcccgtgct cgacagcgac    1380
ggcagcttct tcctgtactc caagctcacc gtggataagt ccaggtggca gcaaggcaac    1440
gtgtttagct gcagcgtgat gcacgaagct ctccacaacc actataccca gaagtccctc    1500
agcctcagcc ctggcaagta gtga                                           1524
```

<210> SEQ ID NO 8
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Lys Asn Leu Tyr Leu Ser Cys Val Leu Lys Asp Asp Lys Pro Thr
1               5                   10                  15
Leu Gln Leu Glu Ser Val Asp Pro Lys Asn Tyr Pro Lys Lys Lys Met
            20                  25                  30
```

Glu Lys Arg Phe Val Phe Asn Lys Ile Glu Ile Asn Lys Leu Glu
            35                  40                  45

Phe Glu Ser Ala Gln Phe Pro Asn Trp Tyr Ile Ser Thr Ser Gln Ala
 50                  55                  60

Glu Asn Met Pro Val Phe Leu Gly Gly Thr Lys Gly Gly Gln Asp Ile
 65                  70                  75                  80

Thr Asp Phe Thr Met Gln Phe Val Ser Ser Gly Gly Ser Gly Gly Ser
                 85                  90                  95

Gly Ala Pro Val Arg Ser Leu Asn Cys Thr Leu Arg Asp Ser Gln Gln
            100                 105                 110

Lys Ser Leu Val Met Ser Gly Pro Tyr Glu Leu Lys Ala Leu His Leu
            115                 120                 125

Gln Gly Gln Asp Met Glu Gln Gln Val Val Phe Ser Met Ser Phe Val
130                 135                 140

Gln Gly Glu Glu Ser Asn Asp Lys Ile Pro Val Ala Leu Gly Leu Lys
145                 150                 155                 160

<210> SEQ ID NO 9
<211> LENGTH: 486
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gagaagaacc tctacctctc ctgcgtgctg aaggacgaca gcccacact ccagctggag      60 tccgtggacc ccaagaacta ccccaagaag aagatggaga gcggttcgt gttcaacaag     120 atcgagatca caacaagct ggagttcgag agcgcccagt tccccaactg gtacatttcc     180
acctcccagg ccgagaacat gcccgtcttt ctgggcggaa ccaagggcgg ccaggacatc     240
accgacttca ccatgcagtt cgtctccagc ggaggaagcg gaggcagcgg agctcccgtg     300
aggagcctga actgcaccct gagggacagc cagcagaagt ccctggtgat gtccggaccc     360
tacgaactga aggccctcca tctgcaagga caggatatgg agcagcaggt ggtgttctcc     420
atgtccttcg tccagggcga agagtccaac gacaagatcc ccgtggccct gggcctgaaa     480
tagtga                                                                486

<210> SEQ ID NO 10
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Ala Met Lys Arg Gly Leu Cys Cys Val Leu Leu Leu Cys Gly
  1               5                  10                  15

Ala Val Phe Val Ser Ala Arg Asp Tyr Lys Asp Asp Asp Asp Lys Asp
             20                  25                  30

Lys Cys Lys Glu Arg Glu Glu Lys Ile Ile Leu Val Ser Ser Ala Asn
             35                  40                  45

Glu Ile Asp Val Arg Pro Cys Pro Leu Asn Pro Asn Glu His Lys Gly
 50                  55                  60

Thr Ile Thr Trp Tyr Lys Asp Asp Ser Lys Thr Pro Val Ser Thr Glu
 65                  70                  75                  80

Gln Ala Ser Arg Ile His Gln His Lys Glu Lys Leu Trp Phe Val Pro
            85                  90                  95

Ala Lys Val Glu Asp Ser Gly His Tyr Tyr Cys Val Val Arg Asn Ser
        100                 105                 110

Ser Tyr Cys Leu Arg Ile Lys Ile Ser Ala Lys Phe Val Glu Asn Glu
    115                 120                 125

Pro Asn Leu Cys Tyr Asn Ala Gln Ala Ile Phe Lys Gln Lys Leu Pro
130                 135                 140

Val Ala Gly Asp Gly Gly Leu Val Cys Pro Tyr Met Glu Phe Phe Lys
145                 150                 155                 160

Asn Glu Asn Asn Glu Leu Pro Lys Leu Gln Trp Tyr Lys Asp Cys Lys
                165                 170                 175

Pro Leu Leu Leu Asp Asn Ile His Phe Ser Gly Val Lys Asp Arg Leu
            180                 185                 190

Ile Val Met Asn Val Ala Glu Lys His Arg Gly Asn Tyr Thr Cys His
        195                 200                 205

Ala Ser Tyr Thr Tyr Leu Gly Lys Gln Tyr Pro Ile Thr Arg Val Ile
    210                 215                 220

Glu Phe Ile Thr Leu Glu Glu Asn Ser Gly Ser Gly Asn Lys Leu
225                 230                 235                 240

Glu Phe Glu Ser Ala Gln Phe Pro Asn Trp Tyr Ile Ser Thr Ser Gln
                245                 250                 255

Ala Glu Asn Met Pro Val Phe Leu Gly Gly Thr Lys Gly Gly Gln Asp
            260                 265                 270

Ile Thr Asp Phe Thr Met Gln Phe Val Ser Ser Gly Ser Gly Gly
        275                 280                 285

Ser Gly Ala Pro Val Arg Ser Leu Asn Cys Thr Leu Arg Asp Ser Gln
    290                 295                 300

Gln Lys Ser Leu Val Met Ser Gly Pro Tyr Glu Leu Lys Ala Leu His
305                 310                 315                 320

Leu Gln Gly Gln Asp Met Glu Gln Gln Val Val Phe Ser Met Ser Phe
                325                 330                 335

Val Gln Gly Glu Glu Ser Asn Asp Lys Ile Pro Val Ala Leu Gly Leu
            340                 345                 350

Lys Glu Lys Asn Leu Tyr Leu Ser Cys Val Leu Lys Asp Asp Lys Pro
        355                 360                 365

Thr Leu Gln Leu Glu Ser Val Asp Pro Lys Asn Tyr Pro Lys Lys Lys
    370                 375                 380

Met Glu Lys Arg Phe Val Phe Asn Lys Ile Glu Ile Asn
385                 390                 395

<210> SEQ ID NO 11
<211> LENGTH: 1197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atggacgcta tgaagcgggg actgtgctgc gtgctcctgc tgtgcggcgc tgtctttgtc      60
agcgcccggg actataagga cgatgatgac aaggacaagt gcaaggagcg ggaggagaag     120
atcatcctgg tgagctccgc caacgagatt gacgtcggc cctgccctct caaccccaac      180
gagcataagg gcaccatcac ctggtacaaa gacgacagca aaacccgt ctccaccgag       240

```
caagcctccc ggattcacca gcacaaggag aagctctggt tcgtgcccgc taaggtggag      300
gattccggac actactactg tgtggtccgg aactccagct actgcctgag gattaagatc      360
agcgctaagt tcgtcgagaa cgagcccaac ctctgctaca atgcccaggc catcttcaag      420
cagaagctcc ctgtggctgg agacggaggc ctggtctgcc cctacatgga gttcttcaag      480
aacgagaata cgagctgcc taagctgcag tggtacaagg actgcaaacc cctgctcctc       540
gacaacatcc acttctccgg cgtcaaggac cggctgatcg tcatgaacgt ggccgagaag      600
cacaggggca actatacctg tcacgccagc tacacctacc tgggaaagca gtatcctatc      660
accagggtga ttgagttcat cacactcgag gaaaacagcg gcggcagcgg caacaagctg      720
gagttcgagt ccgcccagtt tcctaactgg tacatctcca agccaggc cgagaacatg        780 cctgtcttcc tgggcggcac caaggcggc caagatatca ccgacttcac catgcagttt       840
gtgagctccg gaggctccgg aggaagcgga gctcctgtgc ggtccctgaa ttgcaccctg      900
cgggattccc aacagaagag cctggtgatg tccggcccct acgagctcaa ggccctccat      960
ctgcaaggcc aggacatgga gcagcaggtg gtcttcagca tgagcttcgt gcagggagag     1020
gagtccaacg ataagatccc cgtcgctctc ggactcaagg agaagaacct gtacctctcc     1080
tgcgtgctga aggacgataa gcccacctc cagctggaat ccgtggaccc caagaactac      1140
cccaagaaaa aaatggaaaa gcggtttgtc tttaacaaga tcgagattaa ctagtga       1197

<210> SEQ ID NO 12
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
                20                  25                  30

Tyr Ala Asp Glu Thr Ala Thr Ile Val Glu Phe Leu Asn Arg Trp Ile
            35                  40                  45

Thr Phe Cys Gln Ser Ile Ile Ser Thr Leu Thr Gly Gly Ser Ser Ser
        50                  55                  60

Thr Lys Lys Thr Gln Leu Gln Leu Glu His Leu Leu Asp Leu Gln
65                  70                  75                  80

Met Ile Leu Asn Gly Ile Asn Asn Tyr Lys Asn Pro Lys Leu Thr Arg
                85                  90                  95

Met Leu Thr Phe Lys Phe Tyr Met Pro Lys Lys Ala Thr Glu Leu Lys
            100                 105                 110

His Leu Gln Cys Leu Glu Glu Glu Leu Lys Pro Leu Glu Glu Val Leu
        115                 120                 125

Asn Leu Ala Gln Gly Ser Gly Gly Gly Ser Glu Leu Cys Asp Asp Asp
    130                 135                 140

Pro Pro Glu Ile Pro His Ala Thr Phe Lys Ala Met Ala Tyr Lys Glu
145                 150                 155                 160

Gly Thr Met Leu Asn Cys Glu Cys Lys Arg Gly Phe Arg Arg Ile Lys
                165                 170                 175

Ser Gly Ser Leu Tyr Met Leu Cys Thr Gly Asn Ser Ser His Ser Ser
            180                 185                 190
```

Trp Asp Asn Gln Cys Gln Cys Thr Ser Ser Ala Thr Arg Asn Thr Thr
            195                 200                 205

Lys Gln Val Thr Pro Gln Pro Glu Glu Gln Lys Glu Arg Lys Thr Thr
    210                 215                 220

Glu Met Gln Ser Pro Met Gln Pro Val Asp Gln Ala Ser Leu Pro Gly
225                 230                 235                 240

His Cys Arg Glu Pro Pro Pro Trp Asn Glu Ala Thr Glu Arg Ile
            245                 250                 255

Tyr His Phe Val Val Gly Gln Met Val Tyr Gln Cys Val Gln Gly
            260                 265                 270

Tyr Arg Ala Leu His Arg Gly Pro Ala Glu Ser Val Cys Lys Met Thr
            275                 280                 285

His Gly Lys Thr Arg Trp Thr Gln Pro Gln Leu Ile Cys Thr Gly Gly
            290                 295                 300

Gly Gly Ser Glu Pro Lys Ser Ser Asp Lys Thr His Thr Cys Pro Pro
305                 310                 315                 320

Cys Pro Ala Pro Glu Leu Leu Gly Gly Pro Ser Val Phe Leu Phe Pro
                325                 330                 335

Pro Lys Pro Lys Asp Thr Leu Met Ile Ser Arg Thr Pro Glu Val Thr
            340                 345                 350

Cys Val Val Val Asp Val Ser His Glu Asp Pro Glu Val Lys Phe Asn
            355                 360                 365

Trp Tyr Val Asp Gly Val Glu Val His Asn Ala Lys Thr Lys Pro Arg
            370                 375                 380

Glu Glu Gln Tyr Asn Ser Thr Tyr Arg Val Val Ser Val Leu Thr Val
385                 390                 395                 400

Leu His Gln Asp Trp Leu Asn Gly Lys Glu Tyr Lys Cys Lys Val Ser
                405                 410                 415

Asn Lys Ala Leu Pro Ala Pro Ile Glu Lys Thr Ile Ser Lys Ala Lys
            420                 425                 430

Gly Gln Pro Arg Glu Pro Gln Val Tyr Thr Leu Pro Pro Ser Arg Glu
            435                 440                 445

Glu Met Thr Lys Asn Gln Val Ser Leu Thr Cys Leu Val Lys Gly Phe
            450                 455                 460

Tyr Pro Ser Asp Ile Ala Val Glu Trp Glu Ser Asn Gly Gln Pro Glu
465                 470                 475                 480

Asn Asn Tyr Lys Thr Thr Pro Pro Val Leu Asp Ser Asp Gly Ser Phe
            485                 490                 495

Phe Leu Tyr Ser Lys Leu Thr Val Asp Lys Ser Arg Trp Gln Gln Gly
                500                 505                 510

Asn Val Phe Ser Cys Ser Val Met His Glu Ala Leu His Asn His Tyr
            515                 520                 525

Thr Gln Lys Ser Leu Ser Leu Ser Pro Gly Lys
            530                 535

<210> SEQ ID NO 13
<211> LENGTH: 1623
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tccaagaact tccacctgag gcctcgggac ctgatctcca acatcaacgt gatcgtgctg    60

```
gaactgaagg gctccgagac aaccttcatg tgcgagtacg ccgacgagac agctaccatc      120
gtggaatttc tgaaccggtg gatcaccttc tgccagtcca tcatctccac cctgaccggc      180
ggctcctcca gcaccaagaa acccagctg cagctggaac atctgctgct ggacctgcag       240
atgatcctga acggcatcaa caactacaag aaccccaagc tgacccggat gctgaccttc      300
aagttctaca tgcccaagaa ggccaccgaa ctgaaacatc tgcagtgcct ggaagaagaa      360
ctgaagcccc tggaagaggt gctgaacctg gctcagggat ctggcggcgg atctgagctg      420
tgcgacgacg accctcctga gatccctcac gccaccttca aggccatggc ttacaaagag      480
ggcaccatgc tgaactgcga gtgcaagaga ggcttccggc ggatcaagtc cggctccctg      540
tacatgctgt gcaccggcaa ctccagccac tcctcctggg acaaccagtg ccagtgcacc      600
tcctctgcca cccggaacac caccaaacaa gtgaccccccc agcccgagga acagaaagag      660
cgcaagacca ccgagatgca gtcccccatg cagcctgtgg accaggcttc tctgcctggc      720
cactgcagag agcctccacc ttgggagaac gaggctaccg agagaatcta ccacttcgtc      780
gtgggccaga tggtgtacta ccagtgcgtg cagggctacc gcgccctgca tagaggacct      840
gctgagtccg tgtgcaagat gacccacggc aagacccggt ggaccagcc tcagctgatc       900 tgtacaggcg gcggaggctc cgagcctaag tcctccgata agacccacac ctgtccccccc     960 tgtcctgccc ctgaactgct gggaggccct tccgtgttcc tgttccccccc aaagcccaag    1020 gacaccctga tgatctcccg gacccccgaa gtgacctgcg tggtggtgga tgtgtcccac     1080
gaggaccctg aagtgaagtt caattggtac gtggacggcg tggaagtgca caacgccaag     1140
accaagccca gagaggaaca gtacaactcc acctaccggg tggtgtccgt gctgaccgtg     1200
ctgcaccagg attggctgaa tggcaaagag tacaagtgca aggtgtccaa caaggccctg     1260
ccagccccca tcgaaaagac catctccaag gccaagggcc agccccggga accccaggtg     1320
tacacactgc cccctagccg ggaagagatg accaagaacc aggtgtccct gacctgtctc     1380
gtgaagggct tctaccccttc cgatatcgcc gtggaatggg agtccaacgg ccagcctgag    1440
aacaattata agaccacccc ccctgtgctg gactccgacg gctcattctt cctgtacagc     1500
aagctgacag tggacaagtc ccggtggcag cagggcaacg tgttctcctg ctccgtgatg     1560
cacgaggccc tgcacaacca ctacacccag aagtccctgt ccctgtctcc cggcaagtga    1620
tga                                                                   1623
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Gly Ser Gly Gly Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Gly Gly Ser Gly Gly Ser Gly
1               5

<210> SEQ ID NO 16
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly
1

<210> SEQ ID NO 17
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Gly
1

<210> SEQ ID NO 18
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Gly Gly
1

<210> SEQ ID NO 19
<211> LENGTH: 269
<212> TYPE: PRT
<213> ORGANISM: Homo sapiens

<400> SEQUENCE: 19

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
```

```
            130                 135                 140
Leu His Leu Gln Gly Gln Asp Met Glu Gln Gln Val Val Phe Ser Met
145                 150                 155                 160

Ser Phe Val Gln Gly Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
                195                 200                 205

Lys Lys Met Glu Lys Arg Phe Val Phe Asn Lys Ile Glu Ile Asn Asn
                210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265
```

<210> SEQ ID NO 20
<211> LENGTH: 153
<212> TYPE: PRT
<213> ORGANISM: Homo sapiens

<400> SEQUENCE: 20

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
                35                  40                  45

Asn Asn Tyr Lys Asn Pro Lys Leu Thr Arg Met Leu Thr Phe Lys Phe
                50                  55                  60

Tyr Met Pro Lys Lys Ala Thr Glu Leu Lys His Leu Gln Cys Leu Glu
65              70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
                115                 120                 125

Asp Glu Thr Ala Thr Ile Val Glu Phe Leu Asn Arg Trp Ile Thr Phe
                130                 135                 140

Cys Gln Ser Ile Ile Ser Thr Leu Thr
145                 150
```

<210> SEQ ID NO 21
<211> LENGTH: 918
<212> TYPE: PRT
<213> ORGANISM: Homo sapiens

<400> SEQUENCE: 21

```
Met Leu Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
```

```
                35                  40                  45
Val Leu Lys Glu Lys Cys Met Asp Tyr Phe His Val Asn Ala Asn Tyr
 50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ile Ser Gly Leu Pro Pro Glu Lys
                115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
                195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
                275                 280                 285

Leu Lys Pro Phe Thr Glu Tyr Val Phe Arg Ile Arg Cys Met Lys Glu
                290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
                355                 360                 365

Thr Leu Thr Arg Trp Lys Ser His Leu Gln Asn Tyr Thr Val Asn Ala
                370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
                435                 440                 445

Ser Val Lys Lys Tyr Ile Leu Glu Trp Cys Val Leu Ser Asp Lys Ala
                450                 455                 460
```

```
Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
            485                 490                 495

Thr Pro Val Tyr Ala Asp Gly Pro Gly Ser Pro Glu Ser Ile Lys Ala
        500                 505                 510

Tyr Leu Lys Gln Ala Pro Pro Ser Lys Gly Pro Thr Val Arg Thr Lys
    515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880
```

Thr Glu Gly Gln Val Glu Arg Phe Glu Thr Val Gly Met Glu Ala Ala
                    885                 890                 895

Thr Asp Glu Gly Met Pro Lys Ser Tyr Leu Pro Gln Thr Val Arg Gln
                900                 905                 910

Gly Gly Tyr Met Pro Gln
            915

<210> SEQ ID NO 22
<211> LENGTH: 569
<212> TYPE: PRT
<213> ORGANISM: Homo sapiens

<400> SEQUENCE: 22

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Asn Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

```
His Met Ile Gly Ile Cys Val Thr Leu Thr Val Ile Val Cys Ser
            340                 345                 350

Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
                420                 425                 430

Gly Glu Asp Ile Val Glu Val Ile Asn Glu Asn Val Lys Lys Ser Arg
                435                 440                 445

Arg Leu Ile Ile Ile Leu Val Arg Glu Thr Ser Ser Phe Ser Trp Leu
450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
                500                 505                 510

Ile Arg Trp Ser Gly Asp Phe Thr Gln Gly Pro Gln Ser Ala Lys Thr
                515                 520                 525

Arg Phe Trp Lys Asn Val Arg Tyr His Met Pro Val Gln Arg Arg Ser
                530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 23
<211> LENGTH: 272
<212> TYPE: PRT
<213> ORGANISM: Homo sapiens

<400> SEQUENCE: 23

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
```

```
                130               135               140
Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
                180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
        210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 24
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
            20                  25                  30

Tyr Ala Asp Glu Thr Ala Thr Ile Val Glu Phe Leu Asn Arg Trp Ile
        35                  40                  45

Thr Phe Ser Gln Ser Ile Ile Ser Thr Leu Thr Gly Gly Ser Ser Ser
    50                  55                  60

Thr Lys Lys Thr Gln Leu Gln Leu Glu His Leu Leu Leu Asp Leu Gln
65                  70                  75                  80

Met Ile Leu Asn Gly Ile Asn Asn Tyr Lys Asn Pro Lys Leu Thr Arg
                85                  90                  95

Met Leu Thr Phe Lys Phe Tyr Met Pro Lys Lys Ala Thr Glu Leu Lys
            100                 105                 110

His Leu Gln Cys Leu Glu Glu Glu Leu Lys Pro Leu Glu Glu Val Leu
        115                 120                 125

Asn Leu Ala Gln Gly Ser Asp Tyr Lys Asp Asp Asp Lys
    130                 135                 140

<210> SEQ ID NO 25
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
```

```
                    20                  25                  30
Tyr Ala Asp Glu Thr Ala Thr Ile Val Glu Phe Leu Asn Arg Trp Ile
                35                  40                  45
Thr Phe Ser Gln Ser Ile Ile Ser Thr Leu Thr Gly Gly Ser Ser Ser
            50                  55                  60
Thr Lys Lys Thr Gln Leu Gln Leu Glu His Leu Leu Asp Leu Gln
 65                 70                  75                  80
Met Ile Leu Asn Gly Ile Asn Asn Tyr Lys Asn Pro Lys Leu Thr Arg
                85                  90                  95
Met Leu Thr Phe Lys Phe Tyr Met Pro Lys Lys Ala Thr Glu Leu Lys
                100                 105                 110
His Leu Gln Cys Leu Glu Glu Glu Leu Lys Pro Leu Glu Glu Val Leu
            115                 120                 125
Asn Leu Ala Gln Gly Ser Gly Gly Ser Glu Leu Cys Asp Asp Asp
            130                 135                 140
Pro Pro Glu Ile Pro His Ala Thr Phe Lys Ala Met Ala Tyr Lys Glu
145                 150                 155                 160
Gly Thr Met Leu Asn Cys Glu Cys Lys Arg Gly Phe Arg Arg Ile Lys
                165                 170                 175
Ser Gly Ser Leu Tyr Met Leu Cys Thr Gly Asn Ser Ser His Ser Ser
                180                 185                 190
Trp Asp Asn Gln Cys Gln Cys Thr Ser Ser Ala Thr Arg Asn Thr Thr
            195                 200                 205
Lys Gln Val Thr Pro Gln Pro Glu Glu Gln Lys Glu Arg Lys Thr Thr
            210                 215                 220
Glu Met Gln Ser Pro Met Gln Pro Val Asp Gln Ala Ser Leu Pro Gly
225                 230                 235                 240
His Cys Arg Glu Pro Pro Pro Trp Glu Asn Glu Ala Thr Glu Arg Ile
                245                 250                 255
Tyr His Phe Val Val Gly Gln Met Val Tyr Tyr Gln Cys Val Gln Gly
                260                 265                 270
Tyr Arg Ala Leu His Arg Gly Pro Ala Glu Ser Val Cys Lys Met Thr
            275                 280                 285
His Gly Lys Thr Arg Trp Thr Gln Pro Gln Leu Ile Cys Thr Gly Gly
            290                 295                 300
Gly Gly Ser Glu Pro Lys Ser Ser Asp Lys Thr His Thr Cys Pro Pro
305                 310                 315                 320
Cys Pro Ala Pro Glu Leu Leu Gly Gly Pro Ser Val Phe Leu Phe Pro
                325                 330                 335
Pro Lys Pro Lys Asp Thr Leu Met Ile Ser Arg Thr Pro Glu Val Thr
                340                 345                 350
Cys Val Val Val Asp Val Ser His Glu Asp Pro Glu Val Lys Phe Asn
            355                 360                 365
Trp Tyr Val Asp Gly Val Glu Val His Asn Ala Lys Thr Lys Pro Arg
            370                 375                 380
Glu Glu Gln Tyr Asn Ser Thr Tyr Arg Val Val Ser Val Leu Thr Val
385                 390                 395                 400
Leu His Gln Asp Trp Leu Asn Gly Lys Glu Tyr Lys Cys Lys Val Ser
                405                 410                 415
Asn Lys Ala Leu Pro Ala Pro Ile Glu Lys Thr Ile Ser Lys Ala Lys
                420                 425                 430
Gly Gln Pro Arg Glu Pro Gln Val Tyr Thr Leu Pro Pro Ser Arg Glu
            435                 440                 445
```

```
Glu Met Thr Lys Asn Gln Val Ser Leu Thr Cys Leu Val Lys Gly Phe
    450                 455                 460

Tyr Pro Ser Asp Ile Ala Val Glu Trp Glu Ser Asn Gly Gln Pro Glu
465                 470                 475                 480

Asn Asn Tyr Lys Thr Thr Pro Pro Val Leu Asp Ser Asp Gly Ser Phe
                485                 490                 495

Phe Leu Tyr Ser Lys Leu Thr Val Asp Lys Ser Arg Trp Gln Gln Gly
            500                 505                 510

Asn Val Phe Ser Cys Ser Val Met His Glu Ala Leu His Asn His Tyr
        515                 520                 525

Thr Gln Lys Ser Leu Ser Leu Ser Pro Gly Lys
    530                 535

<210> SEQ ID NO 26
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
            20                  25                  30

Tyr Ala Asp Glu Thr Ala Thr Ile Val Glu Phe Leu Asn Arg Trp Ile
        35                  40                  45

Thr Phe Ser Gln Ser Ile Ile Ser Thr Leu Thr Gly Gly Ser Ser Ser
    50                  55                  60

Thr Lys Lys Thr Gln Leu Gln Leu Glu His Leu Leu Asp Leu Gln
65                  70                  75                  80

Met Ile Leu Asn Gly Ile Asn Asn Tyr Lys Asn Pro Lys Leu Thr Arg
                85                  90                  95

Met Leu Thr Phe Lys Phe Tyr Met Pro Lys Lys Ala Thr Glu Leu Lys
            100                 105                 110

His Leu Gln Cys Leu Glu Glu Glu Leu Lys Pro Leu Glu Glu Val Leu
        115                 120                 125

Asn Leu Ala Gln Gly Ser Gly Gly Ser Glu Leu Cys Asp Asp Asp
    130                 135                 140

Pro Pro Glu Ile Pro His Ala Thr Phe Lys Ala Met Ala Tyr Lys Glu
145                 150                 155                 160

Gly Thr Met Leu Asn Cys Glu Cys Lys Arg Gly Phe Arg Arg Ile Lys
                165                 170                 175

Ser Gly Ser Leu Tyr Met Leu Cys Thr Gly Asn Ser Ser His Ser Ser
            180                 185                 190

Trp Asp Asn Gln Cys Gln Cys Thr Ser Ser Ala Thr Arg Asn Thr Thr
        195                 200                 205

Lys Gln Val Thr Pro Gln Pro Glu Glu Gln Lys Glu Arg Lys Thr Thr
    210                 215                 220

Glu Met Gln Ser Pro Met Gln Pro Val Asp Gln Ala Ser Leu Pro Gly
225                 230                 235                 240

His Cys Arg Glu Pro Pro Pro Trp Glu Asn Glu Ala Thr Glu Arg Ile
                245                 250                 255

Tyr His Phe Val Val Gly Gln Met Val Tyr Tyr Gln Cys Val Gln Gly
```

```
                260             265             270
Tyr Arg Ala Leu His Arg Gly Pro Ala Glu Ser Val Cys Lys Met Thr
            275             280             285
His Gly Lys Thr Arg Trp Thr Gln Pro Gln Leu Ile Cys Thr Gly Asp
        290             295             300
Tyr Lys Asp Asp Asp Asp Lys
305             310

<210> SEQ ID NO 27
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Pro Lys Ser Ser Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Glu Glu Met Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys Gly Ser Ile Thr Cys Pro Pro Pro
225                 230                 235                 240
Met Ser Val Glu His Ala Asp Ile Trp Val Lys Ser Tyr Ser Leu Tyr
                245                 250                 255
Ser Arg Glu Arg Tyr Ile Cys Asn Ser Gly Phe Lys Arg Lys Ala Gly
            260                 265                 270
Thr Ser Ser Leu Thr Glu Cys Val Leu Asn Lys Ala Thr Asn Val Ala
        275                 280                 285
His Trp Thr Thr Pro Ser Leu Lys Cys Ile Arg Asp Gly Gly Ser Glu
    290                 295                 300
```

```
Leu Glu Glu Lys Asn Ile Lys Glu Phe Leu Gln Ser Phe Val His Ile
305                 310                 315                 320

Val Gln Met Phe Ile Asn Gly Gly Gly Ser Asn Trp Val Asn Val Ile
                325                 330                 335

Ser Asp Leu Lys Lys Ile Glu Asp Leu Ile Gln Ser Met His Ile Asp
                340                 345                 350

Ala Thr Leu Tyr Thr Glu Ser Asp Val His Pro Ser Cys Lys Val Thr
            355                 360                 365

Ala Met Lys Cys Phe Leu Leu Glu Leu Gln Val Ile Ser Leu Glu Ser
        370                 375                 380

Gly Asp Ala Ser Ile His Asp Thr Val Glu Asn Leu Ile Ile Leu Ala
385                 390                 395                 400

Asn Asn Ser Leu Ser Ser Asn Gly Asn Val Thr Glu Ser Gly Cys Lys
                405                 410                 415

Glu Cys

<210> SEQ ID NO 28
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Tyr Lys Asp Asp Asp Lys Gly Ser Ile Thr Cys Pro Pro Pro
1               5                   10                  15

Met Ser Val Glu His Ala Asp Ile Trp Val Lys Ser Tyr Ser Leu Tyr
                20                  25                  30

Ser Arg Glu Arg Tyr Ile Cys Asn Ser Gly Phe Lys Arg Lys Ala Gly
            35                  40                  45

Thr Ser Ser Leu Thr Glu Cys Val Leu Asn Lys Ala Thr Asn Val Ala
        50                  55                  60

His Trp Thr Thr Pro Ser Leu Lys Cys Ile Arg Asp Gly Gly Ser Glu
65                  70                  75                  80

Leu Glu Glu Lys Asn Ile Lys Glu Phe Leu Gln Ser Phe Val His Ile
                85                  90                  95

Val Gln Met Phe Ile Asn Gly Gly Gly Ser Asn Trp Val Asn Val Ile
                100                 105                 110

Ser Asp Leu Lys Lys Ile Glu Asp Leu Ile Gln Ser Met His Ile Asp
            115                 120                 125

Ala Thr Leu Tyr Thr Glu Ser Asp Val His Pro Ser Cys Lys Val Thr
        130                 135                 140

Ala Met Lys Cys Phe Leu Leu Glu Leu Gln Val Ile Ser Leu Glu Ser
145                 150                 155                 160

Gly Asp Ala Ser Ile His Asp Thr Val Glu Asn Leu Ile Ile Leu Ala
                165                 170                 175

Asn Asn Ser Leu Ser Ser Asn Gly Asn Val Thr Glu Ser Gly Cys Lys
                180                 185                 190

Glu Cys
```